United States Patent [19]
Finn et al.

[11] Patent Number: 5,744,144
[45] Date of Patent: Apr. 28, 1998

[54] SYNTHETIC MULTIPLE TANDEM REPEAT MUCIN AND MUCIN-LIKE PEPTIDES, AND USES THEREOF

[75] Inventors: Olivera J. Finn; J. Darrell Fontenot, both of Pittsburgh; Ronald C. Montelaro, Wexford, all of Pa.

[73] Assignee: University Of Pittsburgh University Patent Committee Policy And Procedures, Pittsburgh, Pa.

[21] Appl. No.: 99,354

[22] Filed: Jul. 30, 1993

[51] Int. Cl.[6] .................... A61K 39/00; A61K 45/00; A61K 45/05; C07K 1/00
[52] U.S. Cl. .................... 424/277.1; 424/279.1; 424/280.1; 530/350
[58] Field of Search .................... 424/277.1, 279.1, 424/280.1; 530/350

[56] References Cited

FOREIGN PATENT DOCUMENTS 0369816  5/1990  European Pat. Off. ........ C12P 21/08

OTHER PUBLICATIONS

Gendler, et al, 1988, "A highly immunogenic region of . . . " J. Biol. Chem. 263(26):12820–12823.
Jerome, et al, 1991, "Cytotoxic T-lymphocytes derived from . . . " Cancer Research 51:2908–2916.
Bara, et al, 1993, "A fucose residue can mask the muc–1 . . . " Int. J. Cancer 54 ;607–613.
Hareuveni et al., "Vaccination against tumor cells expressing breast cancer epithelial tumor antigen", Proc. Natl. Acad. Sci. USA, vol. 87, pp. 9498–9502, Dec. 1990, Medical Sciences.
Acres et al., "Vaccinia Virus MUC1 . . . Antigen", Journal of Immunotherapy, 14:136–143, 1993.
Ding et al., "Immunogenicity of synthetic peptides . . . MUC1 gene", Cancer Immunol Immunother (1993), 36: 9–17.
S. J. Gendler et al., "Cloning of partial cDNA encoding differentiation and tumor-associated mucin glycoproteins expressed by human mammary epithelium", Proc. Natl. Acad. Sci. USA, vol. 84, pp. 6060–6064, Sep. 1987, Biochemistry.
Nishimori et al., "Influence of Acceptor Substrate Primary Amino Acid . . . N–Acetylgalactosaminyltransferase", The Journal Of Biological Chemistry, The American Society for Biochemistry and Molecular Biology, Inc., vol. 269, No. 23, Issue of Jun. 10, pp. 16123–16130, 1994.
Abstract—"Mucin Based Immunity and Immunotherapy of Cancer", by O.J. Finn, Dept. of Molecular Genetics and Biochemistry, University of Pittsburgh School of Medicine, Pittsburgh, PA 15261, USA.
J. Darrell Fontenot, et al., Biophysical Characterization of One–, Two–, and Three–Tandem Repeats of Human Mucin (muc–1) Protein Core[1], Cancer Research 53, 5386–5394, Nov. 15, 1993.
J. D. Fontenot, et al., Synthesis of Large Multideterminant Peptide Immunogens Using A Poly–Proline β–Turn Helix Motiff, Peptide Research, 330–336, vol. 6, No. (1993).

Yasuo Kotera, et al., Humoral Immunity against a Tandem Repeat Epitope of Human Mucin MUC–1 in Sera from Breast, Pancreatic, and Colon Cancer Patients[1], Advances in Brief, Cancer Research 54, 2856–2860, Jun. 1, 1994.

Olivera J. Finn, Antigen–specific, MHC–unrestricted T cells, Biotherapy 4: 239–249, 1992, Dept. of Molecular Genetics and Biochemistry, University of Pittsburg School of Medicine, Pittsburgh, PA 15261, USA.

Carol Clayberger et al., Peptides Corresponding to the CD8 and CD4 Binding Domains of HLA Molecules Block T Lymphocyte Immune Responses In Vitro[1], pp. 946–951.

Alessandro Sette et al., Peptide Binding To The Most Frequent HLA–A Class I Alleles Measured By Quantitative Molecular Binding Assays, pp. 813–822.

Niklas Ahlborg et al., "B– and T–cell responses in congenic mice to repeat sequences of the malaria antigen Pf332: effects of the number of repeats", Immunology Letters, 40 (1994) 147–155.

Michael N. Starnbach et al., Cells Infected with Yersinia Present an Epitope to Class I MHC–Restricted CTL[1], The Journal of Immunology, pp. 1603–1612.

Thorsten Vogel et al., The Majority of Neutralizing Abs in HIV–1–Infected Patients Recognize Linear V3 Loop Sequences, (1994) The Journal of Immunology, pp. 1895–1904.

Ichiro Yoshino et al., "HER2/neu–derived Peptides Are Shared Antigens among Human Non–Small Cell Lung Cancer and Ovarian Cancer", Cancer Research 54 3387–3390, Jul. 1, 1994.

Jean–Pierre Cabaniols et al., "Dose–dependent T cell tolerance to an immunodominant self peptide", Eur. J. Immunol. 1994 24: 1743–1749.

Gillies Benichou et al., "Limited T Cell Response to Donor MHC Peptides During Allograft Rejection", The Journal of Immunology, pp. 938–945.

*Primary Examiner*—Lynette F. Smith
*Attorney, Agent, or Firm*—Cushman Darby & Cushman IP Group of Pillsbury Madison & Sutro, LLP

[57] ABSTRACT

The present invention relates to novel synthetic muc-1 peptides and muc-1 analogs comprising at least two 20-amino acid tandem repeats of muc-1, wherein said synthetic muc-1 peptide is capable of attaining native conformation in the absence of glycosylation. The invention also relates methods of producing the peptides. The invention further relates to uses of the peptides, such as for vaccines and diagnostic testing.

11 Claims, 14 Drawing Sheets

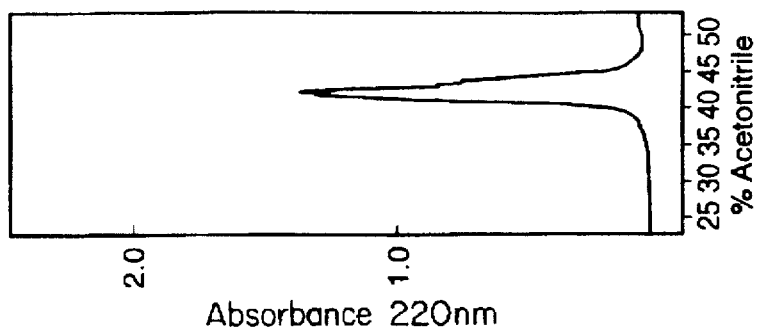
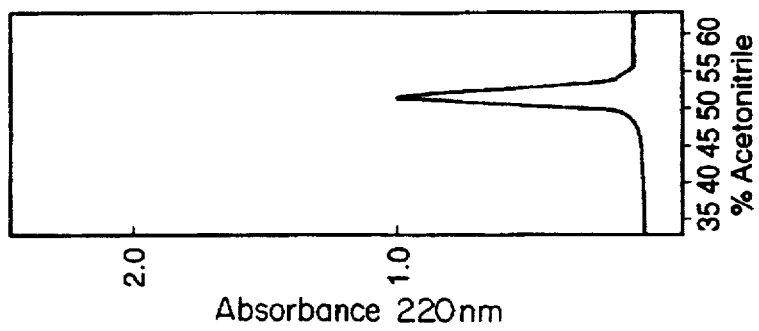
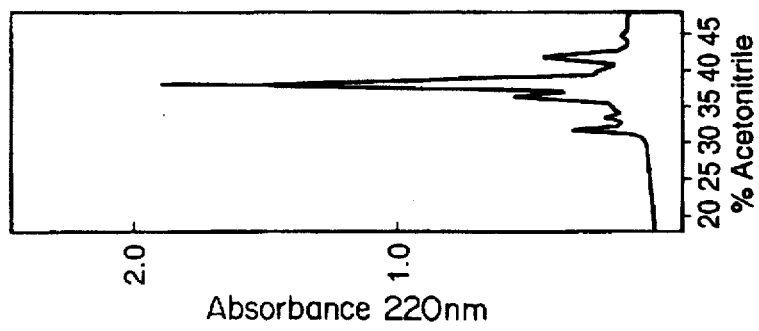
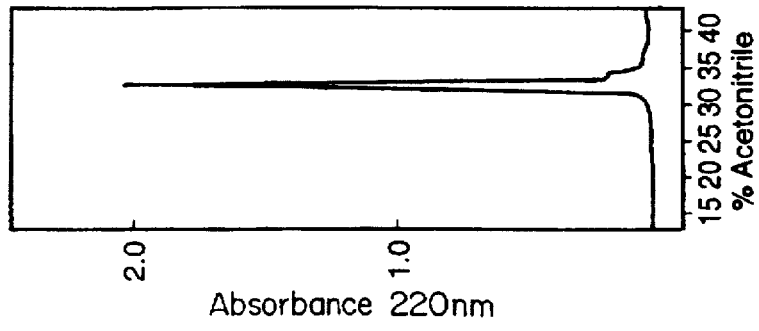

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 40 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala Pro Asp Thr Arg Pro Ala Pro Gly Ser Thr Ala Pro Pro Ala His
1               5                   10                  15

Gly Val Thr Ser Ala Pro Asp Thr Arg Pro Ala Pro Gly Ser Thr Ala
            20                  25                  30

Pro Pro Ala His Gly Val Thr Ser
        35                  40
```

( 2 ) INFORMATION FOR SEQ ID NO:2:

( i ) SEQUENCE CHARACTERISTICS:
( A ) LENGTH: 40 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Xaa Pro Xaa Xaa Xaa Pro Xaa Pro Gly Ser Thr Ala Pro Pro Ala His
1               5                   10                  15

Gly Val Thr Ser Ala Pro Xaa Xaa Xaa Pro Xaa Pro Gly Ser Thr Ala
            20                  25                  30

Pro Pro Ala His Gly Val Thr Ser
        35                  40
```

( 2 ) INFORMATION FOR SEQ ID NO:3:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

```
Pro Asp Thr Arg Pro Ala Pro Ser Thr Ala Pro Pro Ala His Gly Val
1               5                   10                  15

Thr Ser Ala
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gly  Pro  Gly  Arg  Ala  Phe  Pro  Ala  Pro  Ser  Thr  Ala  Pro  Pro  Ala  His
1                  5                            10                           15

Gly  Val  Thr  Ser  Ala
                20
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Pro  Asp  Thr  Arg  Pro  Ala  Pro  Ser  Thr  Ala  Pro  Pro  Ala  Gly  Pro  Gly
1                  5                            10                           15

Arg  Ala  Phe
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Thr  Ala  Glu  Asn  Ala  Glu  Tyr  Leu  Arg  Val
1                  5                          10
```

( 2 ) INFORMATION FOR SEQ ID NO:7:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Thr  Ile  Thr  Pro  Pro  Gln  Ala  Met  Gly  Pro  Asn  Leu  Val  Leu  Pro  Asp
1                  5                            10                           15

Gln  Lys  Pro  Pro  Ser  Arg  Gln  Ser  Gln  Thr  Gly  Ser  Lys  Val  Ala  Thr
                20                            25                           30

Gln  Arg  Pro  Gln  Thr  Asn  Glu  Ser  Ala  Pro  Arg  Ser  Val  Ala  Pro  Thr
                35                            40                           45

Thr  Val  Gly  Pro  Lys  Arg  Ile  Gly  Thr  Gly  Asp  Arg
                50                            55                           60
```

-continued ( 2 ) INFORMATION FOR SEQ ID NO:8:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Thr Pro Pro Gln Ala Met Gly Pro Asn Leu Val Leu Pro Asp Gln Lys
1                5                   10                  15
Pro Pro Ser Arg Gln Ser Gln Thr Gly Ser Lys Val Ala Thr Gln Arg
            20                  25                  30
Pro Gln Thr Asn Glu Ser Ala Pro Arg Ser
        35                  40
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Tyr Pro His Phe Met Pro Thr Asn Leu
1                5
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Tyr Pro His Ala Met Pro Thr Asn Leu Ser
1                5                   10
```

SYNTHETIC MULTIPLE TANDEM REPEAT MUCIN AND MUCIN-LIKE PEPTIDES, AND USES THEREOF

This invention was made with government support under CA-56103 awarded by the National Institutes of Health. The government has certain rights in the invention.

FIELD OF THE INVENTION

The present invention relates to synthetic multiple tandem repeat peptides and methods of synthesizing the peptides. The present invention also relates to uses of the peptides, such as in vaccines and diagnostic tests for human cancers and infectious diseases using the framework structure of the tandemly repeating synthetic peptides.

BACKGROUND INFORMATION

Mucins are large secreted and/or transmembrane glycoproteins with greater than 50% of their molecular weight derived from O-linked carbohydrate attached to serine and threonine residues (for a review see Strouss, G. J. and Dekker, Critical Reviews in Biochemistry and Molecular Biology, 27½: 57–92, 1992). The bulk of the glycosylation is contained within a domain composed of tandemly repeated sequences of 10–81 amino acids per repeat (Gum, et al., J. Biol. Chem., 264: 6480–6487, 1989, Gum, et al. Biochem. Biophys. Res. Commun. 171: 407–415, 1990, Lan, et al., J. Biol. Chem., 265: 15294–15299, 1990, Lan, et al. Cancer Res., 50: 2997–3001, 1990, and Porchet, et al., Biochem. Biophys. Res. Commun., 175: 414–422, 1991). Mucins are produced by cells of epithelial lineage and recently, expression of certain epitopes on one of the mucins, polymorphic epithelial mucin (PEM) encoded by the muc-1 gene, has been identified as being associated with tumors (Hilkens, et al., Cancer Res., 49: 786–793, 1989 and Jerome, et al., Cancer Res., 51: 2908–2915, 1991).

Studies with monoclonal antibodies reactive with epithelial tumors and corresponding normal tissues reveal that there can be different epitopes associated with mucins from malignant cells as opposed to normal cells (Jerome, et al., Cancer Res., 51: 2908–2916, 1991, Girling, et al., Int. J. Cancer, 43: 1072–1076, 1989, Taylor-Papadimitriou, J., Int. J. Cancer, 49: 1–5, 1991). This is in part due to aberrant glycosylation in certain tumors which results in the exposure of the mucin tandem repeat protein core on the cell surface (Hilkens, et al., Cancer Res., 49: 786–793, 1989, Girling, et al., Int. J. Cancer, 43: 1072–1076, 1989, Sell, Progress Path., 21: 1003–1019, 1990, Devine, et al., Cancer Res. 51: 5826–56836, 1991, and Itzkowitz, et al., Gastroenterol., 100: 1691–1700, 1991). The exposure of the protein core of certain mucins found on malignant cells, combined with the ability of the immune system to respond to these structures (Jerome, et al., Cancer Res., 51: 2908–2916, 2916, 1991 and Barnd, et al., PNAS USA, 86: 7159–7163, 1989), offers a unique opportunity to utilize mucin-based vaccines for specific immunotherapy of tumors.

The development of effective vaccine and immunotherapies for human cancers and infectious agents often is dependent on the generation of protective immune responses to specific domains of membrane proteins. Examples include: the tandem repeat (TR) domain of the breast, pancreatic, and ovarian tumor antigen, human mucin muc-1 (Barnd et al., PNAS USA, 86: 7159–7163, 1989; Jerome et al., Cancer Res., 51: 2908–2916, 1991), the principal neutralizing domain of HIV-1 (Javaherian et al., PNAS USA, 86: 6768–6772, 1989; Javaherian et al., Science, 250: 1590–1593, 1990) and the proline rich neutralization domain of the feline leukemia virus external surface unit protein (gp-70) (Nunberg et al., PNAS, 81: 3675–3679, 1984; Elder et al., J. Virol., 61: 8–15, 1987; Strouss et al., J. Virol., 61: 3410–3415, 1987; Nick et al., J. Gen. Virol., 71: 77–83, 1990).

It was recently shown that protein core of the human muc-1 TR domain (Fontenot et al., in press 1993A) and the feline leukemia virus PRN domain of gp-70 (Fontenot et al., in press 1993B) form poly-proline β-turn helixes (Matsushima et al., Function and Genetics, 7: 125–155, 1990). Some common characteristics of the poly-proline β-turn helix include: (1) Approximately 20–60% proline, and a high content of glycine, serine and glutamine: (2) Low predicted α-helix and β-sheet secondary structure content and a high predicted content of βturns: (3) A circular dichroism spectrum consistent with high turn content and low α-helix and β-sheet secondary structure content: (4) Intrinsic viscosity values consistent with the formation of extended rod-shaped structures (Matsushima et al., 1990).

In many cases, the use of the entire glycoprotein as an immunogen for the development of effective vaccines and immunotherapies for human cancers and infectious agents has proven either ineffective due to a lack of immunogenicity, or results in the enhancement of infection and disease due to the inclusion of nonprotective epitopes (Osterhaus et al. Vaccine, 7: 137–141, 1989; Gilbert et al. Virus Research, 7: 49–67, 1987; Burke, D. Perspect. Biol. Med., 35: 511–530, 1992).

The use of synthetic peptides as vaccines can circumvent many of the problems associated with recombinant vaccines. The advantages of the use of synthetic peptides that correspond to specific membrane protein domains include: selection and inclusion of only protective epitopes; exclusion of disease enhancing epitopes and infectious material; and, synthetic peptides antigens are chemically well defined and can be produced at a reasonable cost (Arnon and Horwitz, Curr. Opin. Immunol., 4: 449–453, 1992).

The disadvantages are that small synthetic peptides may not contain the precise amino acid sequences necessary for processing and binding to major histocompatibility complex (MHC) class I and class II proteins, for presentation to the immune system (Rothbard, Biotechnology, 20: 451–465, 1992). Another disadvantage is that the solution structure of small peptides may be different than that found in the native protein and therefore not induce humoral immunity of the proper specificity and affinity to provide protective immunity (Bernard et al. Aids Res. and Hum. Retroviruses, 6: 243–249, 1990).

However, peptide fragments of larger proteins which are rich in proline, peptides containing b-turns, and peptides with proline rich direct sequence repeats have been shown to maintain native structure in solution and be immunogenic (Broekhuijsen et al., J. Gen. Virol., 68: 3137–3145, 1987; Bhandary et al., Int. J. Peptide Protein Res. 36: 122–127, 1990; Dyson et al., J. Mol. Biol., 201: 201–217, 1988; Dyson et al., Biochemistry 31: 1458–1463, 1992; Mayo et al., Biochemistry 30: 8251–8267, 1991; Richman and Reese, Proc. Natl. Acad. Sci. U.S.A., 85: 1662–1666, 1988) and seem to have potential as vaccine candidates. These include the human mucin and tumor antigen (muc-1) tandem repeat (TR) domain (Gendler et al. J. Biol. Chem., 26: 12820–12823, 1988; Lan et al., Cancer Res. 50: 2997–3001, 1990; Barnd et al., Proc. Natl. Acad. Sci. U.S.A., 86: 7159–7163, 1989; Jerome et al., Cancer Res., 51: 2908–2916, 1991), the retroviral proline rich domains of feline leukemia virus gp70 (Donahue et al., J. Virol., 62: 722–731, 1988), murine leukemia virus gp70 (Battini et al., J. Virol., 66: 1468–1475, 1992), and Gibbon ape leukemia virus (Delassus et al., Virology, 53: 205–213, 1989), and the tandem repeats of the H.8 lipoprotein of Neisseria gonorrhoeae (Baehr et al., Mol. Microbiol. 3: 49–55).

The present invention provides methods for synthesizing long peptides having poly-proline β-turn helices, and methods for modifying these synthetic poly-proline helices for the design of new antigens by tandemly repeating important B- or T-cell epitopes or coupling B- and T-cell epitopes to produce antigens of larger sizes.

The invention is based on the novel method of synthesizing very long peptides of multiple tandem repeats having a poly-proline β-turn structural motif, such as human mucin (muc-1) peptides. The peptides of the invention attain native conformation in the absence of glycosylation, reflecting the structure seen in native mucin.

The invention also relates to methods of designing antigens which are able to induce an immune response. This aspect of the invention is based on the previously identified MHC-unrestricted T-cell reactivity against mucin seen in patients with breast and pancreatic adenocarcinomas expressing this protein (Jerome et al., Cancer Res., 51: 2908–2916, 1991; Barnd et al., Proc. Natl. Acad. Sci. U.S.A., 86: 7159–7163, 1989; Jerome et al., Cancer Res., 52: 5985–5990, 1992) in addition to the newly discovered characteristic of the structure of the poly-repeat synthetic mucin peptide. (Fontenot et al., "Biophysical Characterization of One-, Two-, and Three-Tandem Repeats of the Human Mucin (MUC-1) Protein Core," submitted to Cancer Research.)

The poly-repeat mucin peptide allows the removal of several amino acids from the primary epitope of mucin without interfering with the structure of the tandem repeats important for native conformation and for the MHC-unrestricted T-cell reactivity. It is possible to replace the uninterfering amino acids of the mucin epitope with amino acids from epitopes of important antigens allowing an unrestricted T-cell reactivity to the newly designed immunogen.

SUMMARY OF THE INVENTION

The invention relates to a synthetic muc-1 peptide comprising at least two 20-amino acid tandem repeats of muc-1, which synthetic muc-1 peptide is capable of attaining native conformation in the absence of glycosylation. For instance, the synthetic muc-1 peptide may comprise 2, 3, 4, 5 or more tandem repeats of muc-1.

In another embodiment, the invention relates to a synthetic muc-1-like peptide that comprises at least two 20-amino acid tandem repeats of muc-1 and a foreign amino acid sequence, which peptide is capable of attaining native conformation in the absence of glycosylation. For instance, the synthetic muc-1-like peptide may comprise 2, 3, 4, 5 or more tandem repeats of muc-1. The foreign amino acid sequence may be an epitope, such as, for instance an antigenic epitope corresponding to a virus (for example, HIV), a bacteria, a parasite, or cancer (for example, pancreatic cancer, breast cancer, ovarian cancer or colon cancer). Thus, the peptide is muc-1-like, or an analogue of muc-1 where a "foreign" epitope is appropriately inserted to form an immunologically native synthetic antigen.

The synthetic muc-1 and muc-1-like peptides of the present invention may be 40, 60, 80 or, preferably, 105 amino acids in length, or even larger and may be covalently linked to a pharmaceutically acceptable adjuvant.

In a further embodiment, the present invention relates to a method of producing a mucin peptide having at least two tandem repeats, which peptide is capable of attaining native conformation in the absence of glycosylation. The method relates to standard solid state synthesis protocols, with several modifications. Conventional methodology is employed with the following modifications. Synthesis is stopped when the primary sequence reaches 30 amino acids in length. One half of the resin-bound 30 amino acid peptide is then removed. A monitor step is then employed to monitor the completeness of the reaction. The reaction cycle is then continued until the desired length is obtained.

In another embodiment, the present invention relates to a method of producing muc-1-like peptides having at least two tandem repeats and a foreign amino acid sequence, which muc-1-like peptide is capable of attaining native conformation in the absence of glycosylation. The method relates to standard solid state synthesis protocols, with the several modifications mentioned hereinabove. The foreign amino acid sequence may be an epitope.

The invention also relates to the mucin peptide produced by the method the above-described methods, which peptide may be 40, 60, 80 or, preferably, 105 amino acids in length, although longer lengths are possible.

In another embodiment, the present invention relates to an immunogenic composition capable of inducing in a mammal antibodies against an epitope (such as a vaccine), which composition comprises a synthetic muc-1-like peptide. The synthetic muc-1-like peptide comprises at least two 20-amino acid tandem repeats of muc-1 and the amino acid sequence for the epitope, and the synthetic muc-1 peptide is capable of attaining native conformation in the absence of glycosylation. The synthetic muc-1-like peptide may be 40, 60, 80 or, preferably, 105 amino acids in length, although longer lengths are possible.

In a further embodiment, the present invention relates to a method of inhibiting an immune response in a mammal, comprising the step of administering the above-described immunogenic composition to a mammal in an immunogenically effective amount, which epitope is recognized by an autoantibody produced by the mammal.

In yet a further embodiment, the invention relates to a method of detecting the presence of antibodies to a specific disease (for instance, cancer) in a biological test sample, comprising the steps of:

a) contacting the above-described synthetic muc-1 peptide containing an epitope with the biological test sample, which epitope is reactive with antibodies to the disease, under conditions such that a synthetic muc-1 peptide-antibody complex is formed, and b) detecting the formation of the synthetic muc-1 peptide-antibody complex, which complex is indicative of the presence of antibodies to the specific disease.

In another embodiment, the invention relates to a method for inhibiting the growth of cancer cells, comprising the steps of:

a) obtaining antibodies to the tumor cells by injecting a test mammal, for example, a mouse or a rabbit, with the above-described synthetic muc-1 peptide containing an epitope, which epitope is reactive with antibodies to the cancer cells, under conditions such that a synthetic muc-1 peptide-antibody complex is formed, and isolating said antibodies from the complex from the mammal, b) contacting the isolated antibodies from step a) with an agent capable of inhibiting the growth of cancer cells, under such conditions that an antibody-agent complex is formed, and c) contacting the antibody-agent complex from step b) with cancer cells, under such conditions that the antibody-agent complex reacts with cancer cells and inhibits the growth of the cancer cells. The agent may be a radioisotope (for example, Yttrium 90 and Iodine 131), chemical (for example, methotrexate), toxin (for example, ricin or parts thereof), or enzyme.

BRIEF DESCRIPTION OF THE DRAWINGS

FIGS. 8A–H. The analytical HPLC chromatogram of the crude synthetic peptide products of (a) mucin 105 residues (b) PRN60, 60 residues (c) H2D8, 72 residues (d) H2DAS7, 70 residues (E) electrospray mass spectrum of the mucin 105 major fraction (f) electrospray mass spectrum of PRN60 major fraction (g) electrospray mass spectrum of H2D8 major fraction (h) electrospray mass spectrum of H2DAS7 major fraction.

DETAILED DESCRIPTION OF THE INVENTION

The invention is based in part on the discovery that an additional characteristic of the polyproline β-turn helix is the fidelity of synthesis to lengths not previously attained with Fmoc solid phase peptide synthesis (Fields et al., Principles and practice of solid-phase peptide synthesis. In Synthetic Peptides, G. A. Grant, eds., W. H. Freeman and Co., New York, pp. 77–183, 1992). Two additional characteristics of the poly-proline, β-turn helix are: (1) the ability to form an ordered long-lived conformation in solution and the protection of protons while dissolved in $D_2O$ as determined by $^1$H-NMR spectroscopy (Fontenot et al., in press, 1993A & B); and (2) a large negative CD band at about 198 nm in aqueous solution. The absence of two separate negative CD bands at 220 nm and 208 nm and the lack of a positive band at 192 nm rules out α-helical character to either mucin, PRN60 or H2Dmuc7. In addition, no β-sheet structure is evident due to the absence of the negative band at 216 nm and the large positive band between 195 and 200 nm (Woody, Circular Dichoism of Peptides, In "The Peptides: Analysis, Synthesis, Biology," 7: 16–104, 1985; Johnson, Am. Rev. Biophys. Chem., 17: 145–166, 1988).

Previous model peptide studies with the tandem repeat peptide (PKLKL)n concluded that a single negative CD band at 198 nm was indicative of random coil. However, Dukor & Keiderling (Biopolymers, 31: 1747–1761, 1991) have shown that small peptides tend to assume transient left-handed $3_1$-helixes like that found in poly-proline II, which consists of all trans proline (Dukor & Keiderling, Biopolymers, 31: 1747–1761, 1991). Thus, "random coil" peptides display similar conformations and CD spectra as polyproline β-turn helixes but at much lower intensity as demonstrated in FIG. 10. Clearly, the large negative CD band indicates secondary structure rather than the absence of structure.

The two-dimensional ¹H-NMR (COSY) experiment in D₂O (an example is described below) using a 60 amino acid synthetic peptide shows that the mucin tandem repeat domain can fold into a stable structure, and that this structure is capable of sequestering protons from exchange by deuterium for more than 24 hours. In addition, one-dimensional ¹H-NMR experiments in D₂O with the synthetic peptide analogs corresponding to one-, two-, and three-repeats of the tandem repeat domain, show that formation of the structure is occurring with increasing number of repeats.

Figure 3:
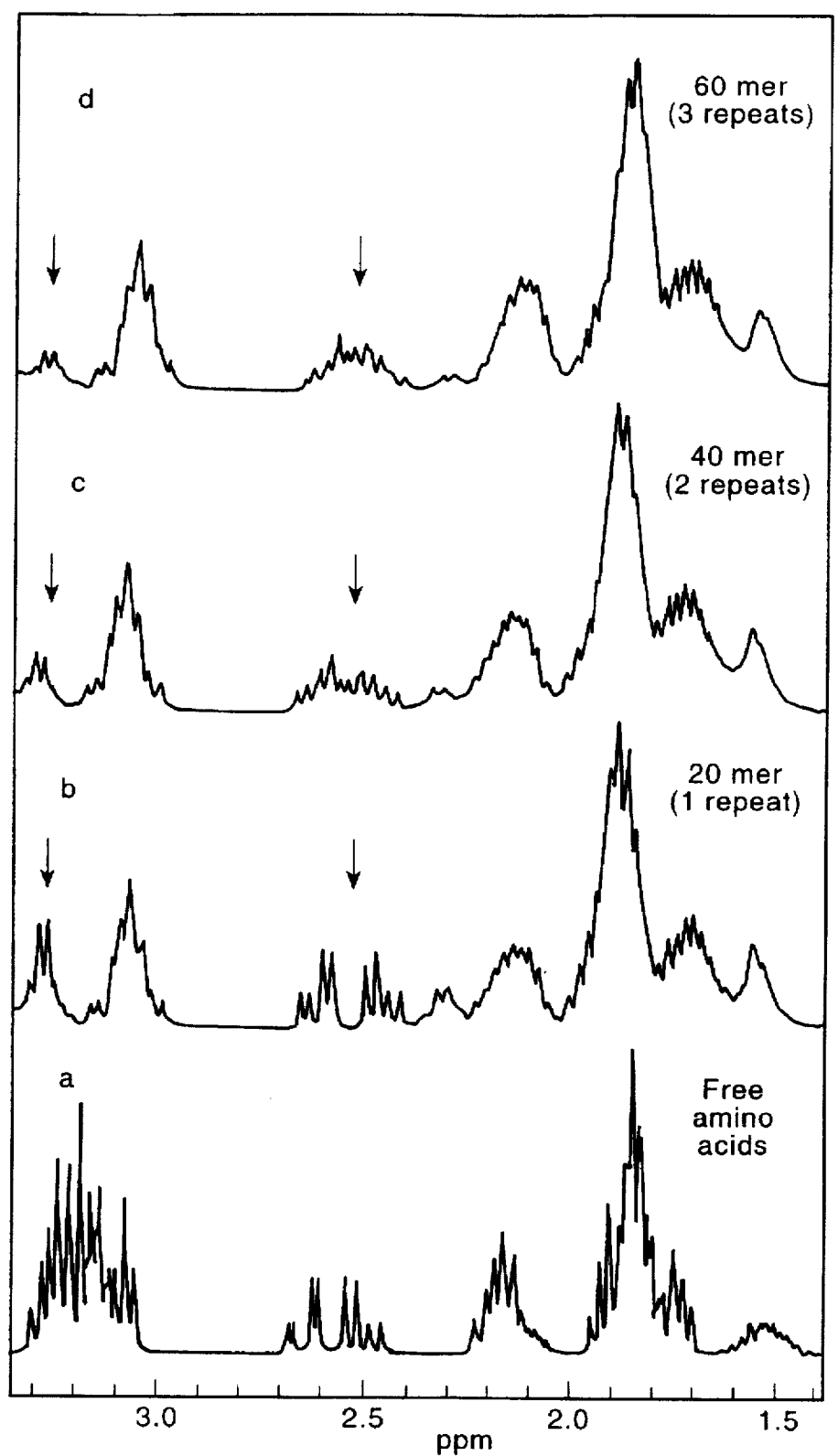
FIGS. 3A–D. $^1$H-NMR spectra of mucin peptides dissolved in deuterated 0.1M phosphate buffer pH 6.89, in $D_2O$ showing the region of the β-protons of aspartic acid and histidine. Development of structure depends on the number of tandem repeats in the peptide.
Figure 4:
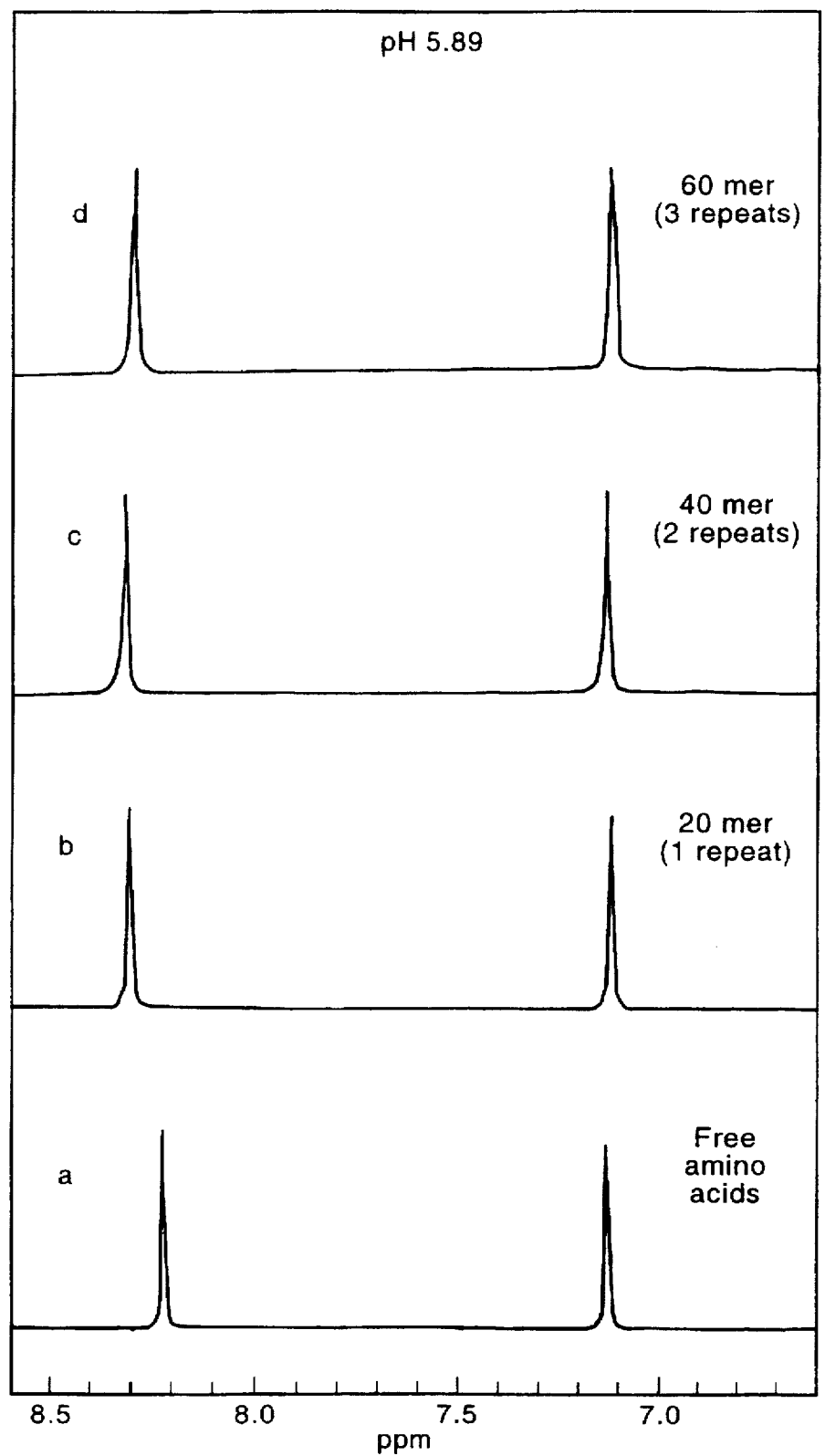
FIGS. 4A–D. $^1$H-NMR spectra of mucin peptides dissolved in deuterated 0.1M phosphate buffer pH 6.89, in $D_2O$ showing the region of the C2 (8.2–8.4 ppm) and C4.
Figure 5:
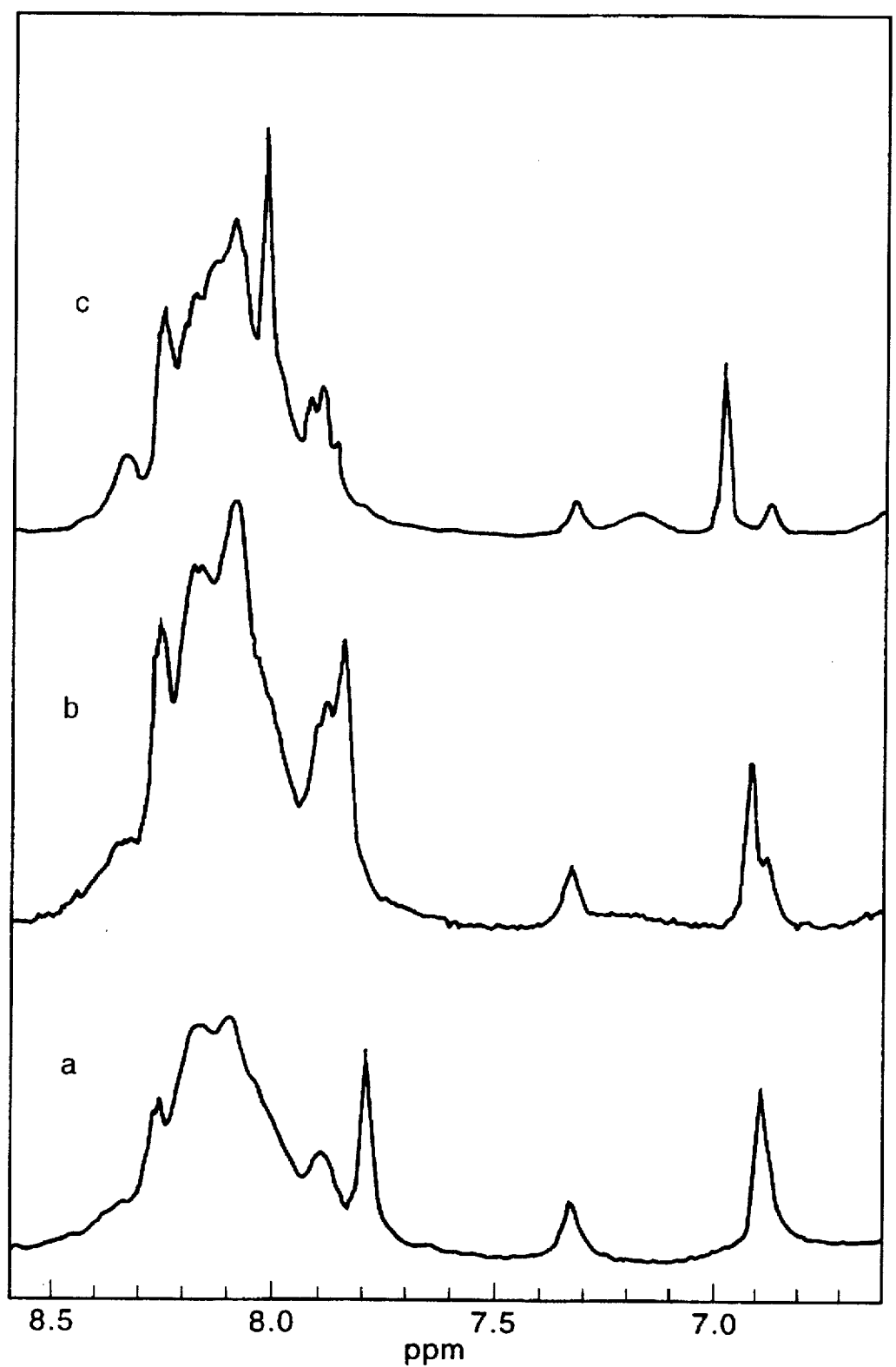
FIGS. 5A–C. $^1$H-NMR spectra of mucin peptides dissolved in $H_2O$ and 0.1M phosphate buffer pH 6.8. (A) twenty amino acid peptide corresponding to one tandem repeat. (B) Forty amino acid peptide corresponding to two tandem repeats. Sixty amino acid peptide corresponding to three tandem repeats.
Figure 6:
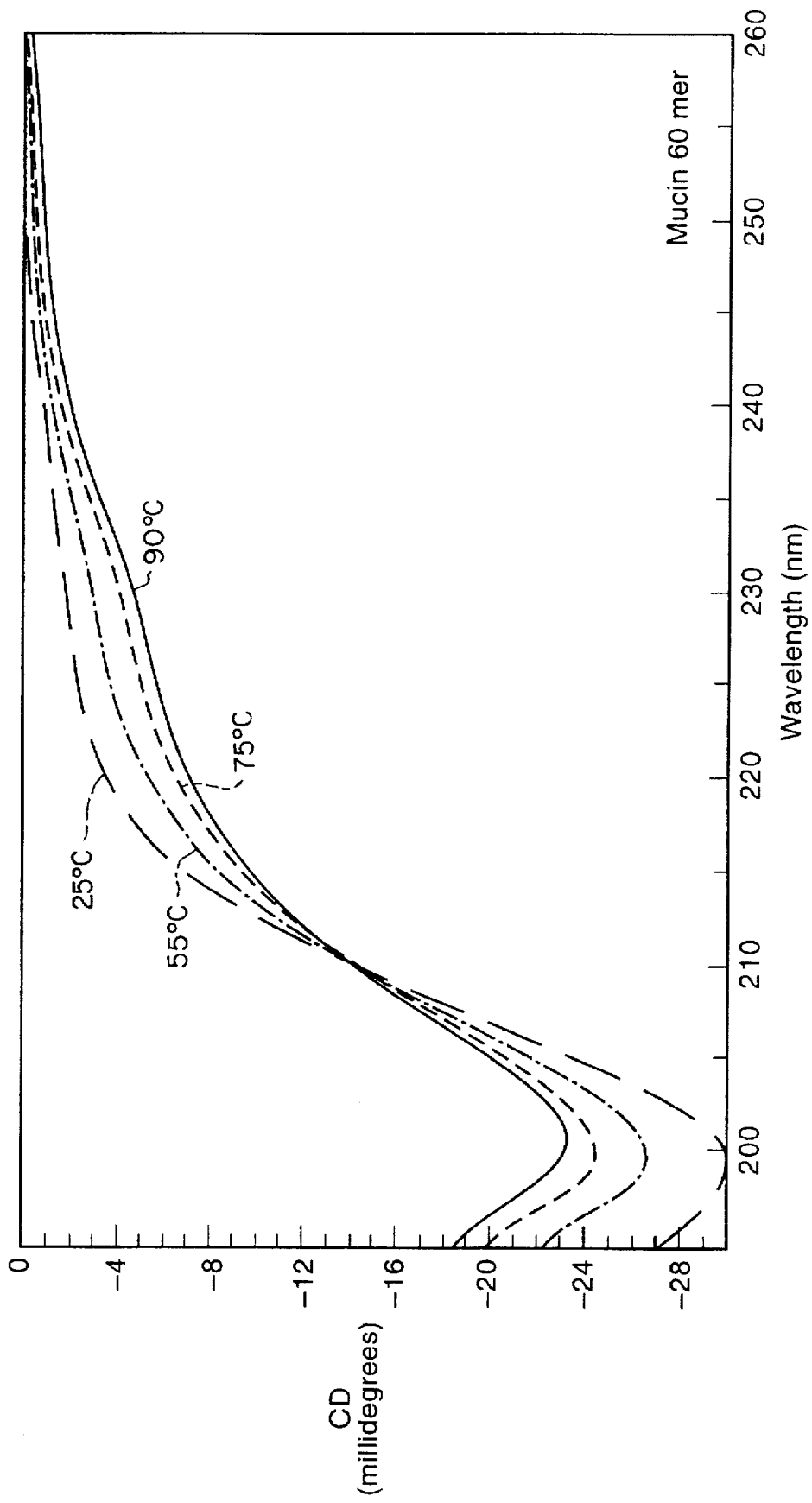
FIG. 6. Circular dichroism spectrum of mucin 60 amino acid peptide in 0.01M phosphate buffer pH 7.2 at 25°, 55°, 75° and 90° C.

The structural changes appear to be occurring throughout the length of the 20 amino acid repeat domain, as changes can be detected throughout the molecule by focusing on the β-protons in the region of 2.4 to 3.3 ppm from DSS (FIG. 3). By concentrating on the β-protons, the inventors have taken advantage of the peculiar repetitive nature of this protein domain. One twenty-amino acid peptide contains all of the protons that can contribute to the ¹HNMR spectrum and any differences observed in the spectrum of peptides corresponding to one-, two-, or three-tandem repeats can only be attributed to changes in the local magnetic environment imposed through the development of secondary structure along the polypeptide backbone. Clearly, the ¹H-NMR spectra reveal that the structures of peptides containing one-, two-, and three-repeats are different. Yet, peptides containing multiple histidyl residues whose C2 and C4 resonances resolve into single peaks suggests that the environment of each histidine in multiple repeat peptides are equivalent. It is believed that the ¹H-NMR results show that the precise conformation of a residue depends on the number of repeats in the peptide.

Previous studies on muc-1 core structure, using an 11-amino acid fragment of muc-1 tandem repeat, were able to show that a reverse-turn structure formed when dissolved in dimethyl sulfoxide, from D2 through P4, and that P4 existed in the trans conformation (Tendler, 1990 and Scanlon, et al., 1992). Using much larger synthetic peptides, the inventors have demonstrated that there is a gradation of structures that depends on the size of the peptide.

This data is strongly supported by the monoclonal antibody binding data. Many of the monoclonal antibodies failed to react with a peptide corresponding to just one repeat, even when the epitope was present, but increasing number of repeats resulted in increased antibody reactivity. This behavior is consistent with that found by other authors which show that providing amino acids C-terminal to the first proline forms the major immunodominant epitope (Price, et al., Molecular Immunology, 27: 795–802, 1990 and Xing, et al., Immunology, 72: 304–311, 1991).

The ¹H-NMR experiments described below clearly show that the mucin tandem repeat domain assumes an ordered structure in solution, and the form of the structure may be further understood by analysis of the mucin sequence, the shape of the molecule obtained from intrinsic viscosity measurements and electron microscopy, and the circular dichroism studies.

In one embodiment, the invention relates to synthetic muc-1 peptides comprising at least two 20-amino acid tandem repeats of muc-1, which synthetic muc-1 peptide is capable of attaining native conformation in the absence of glycosylation. For instance, the muc-1 peptide may comprise 2, 3, 4, 5 or more tandem repeats of muc-1. The synthetic muc-1 peptides of the present invention may be 40, 60, 80 or, preferably, 105 amino acids in length, or even longer, and may be covalently linked to a pharmaceutically acceptable carrier molecule, and may be part of a kit comprising the synthetic muc-1-like peptides and conventional reagents.

Peptide repeats which should be used are those that are poly-proline β-turn helixes. Some common characteristics of peptides having poly-proline β-turn helixes include:

1. Approximately 20–60% proline, and a high content of glycine, serine and glutamine;

2. Low predicted a-helix and b-sheet secondary structure content and a high predicted content of b-turns;

3. A circular dichroism spectrum consistent with high turn content and low a-helix and b-sheet secondary structure content;

4. Intrinsic viscosity values consistent with the formation of extended rod-shaped structures (Matsushima et al. Proteins: Structure, Function and Genetics 7: 125–155, 1990).

Examples of sequences of peptides which can be synthesized by RAMPS are shown in Table 1. The naturally occurring mucin tandem repeat is shown in Table 1, No. 1. The entire proline rich neutralization domain of Feline leukemia virus and a 42 amino acid N-terminal fragment of this domain is shown in Table 1, No. 2, and 3 respectively. Other mucin peptides, such as muc-2, muc-3, or muc-6, are tandem repeats of various lengths. Although these mucin peptides do not have all the same characteristics of muc-1, regions of their sequences can be replaced, such as by proline. Thus, the natural length of the tandem repeat of each particular mucin may be preserved.

In another embodiment, the invention relates to a synthetic muc-1-like peptide that comprises at least two 20-amino acid tandem repeats of muc-1 and a foreign amino acid sequence, which peptide is capable of attaining native conformation in the absence of glycosylation. For instance, the muc-1-like peptide may comprise 2, 3, 4, 5 or more tandem repeats of muc-1. The foreign amino acid sequence may be an epitope, such as, for instance, an antigenic epitope corresponding to a virus (for example, HIV), a bacteria, a parasite, or cancer (for example, pancreatic cancer, breast cancer, ovarian cancer or colon cancer).

The synthetic muc-1-like peptides of the present invention may be 40, 60, 80 or, preferably, 105 amino acids in length, and may be covalently linked to a pharmaceutically acceptable carrier adjuvant, and may be part of a kit comprising the synthetic muc-1-like peptides and conventional reagents.

In a further embodiment, the present invention relates to a method of producing a mucin peptide having at least two tandem repeats, which peptide is capable of attaining native conformation in the absence of glycosylation. The method relates to standard solid state synthesis protocols, with several modifications.

Conventional methodology is employed with the following modifications. Synthesis is stopped when the primary sequence reaches 30 amino acids in length. One half of the resin-bound 30 amino acid peptide is then removed. A monitoring step is then employed to monitor the completeness of the reaction. Then, the reaction cycle is continued until the desired length of peptide is obtained.

The method comprises the steps of:

i) activating an amino acid of interest;

ii) introducing the activated amino acid of interest to appropriate solid phase;

iii) reacting under appropriate conditions until completion;

iv) monitoring for completeness of reaction;

v) repeating steps i) to iv) with the next amino acid of interest, until a 30 amino acid peptide is obtained, at which point half of the 30 amino acid peptide is removed; and vi) continuing the reaction cycle until a mucin peptide of desired length having at least two tandem repeats and capable of attaining native conformation in the absence of glycosylation is formed.

By way of example, the method of the present invention may be achieved by the following protocol, using manual methodology on a Rapid Multiple Peptide Synthesizer (RaMPS).

The Coupling Reaction 0.25 mmole of the appropriate OPfp or Odhbt amino acid ester is dissolved in 1 ml of DMF and added to a standard RaMPS resin cartridge. 0.2 ml of 0.5M 1-hydroxybenzotriazole (HOBT) in DMF is added to the cartridge. 2 ml of DMF is used to rinse the remaining OPfp ester from the amino acid vial into the RaMPS resin cartridge. After the cartridge is capped securely, it is shaken for 2 hours at room temperature.

The RaMPS processor is then turned off, and the cartridge uncapped, opened and drained. The solvent is aspirated under a vacuum.

The resin is soaked for 30–45 sec with DMF, drained and aspirated. This is repeated twice. (3 cycles total)

Next, the resin is soaked for 30–45 sec with Methanol, drained, and aspirated. This is repeated. (2 cycles total)

Next, the reaction is monitored for completeness using the Kaiser or Isatin Test. If the coupling was incomplete, the next step is to be done and the first 4 steps are repeated (through the soaking of the resin in methanol for 30–45 seconds, draining and aspirating). If coupling was complete, the next step is to be done.

The resin is soaked for 30–45 sec with DMF, drained and aspirated. This is repeated three times. (4 cycles total)

The resin is then soaked 30–45 sec with 50% piperidine/DMF, and drained.

Then the RaMPS cartridge valve is closed, and 3 ml 50% piperidine/DMF is added. The cartridge is capped and shaken for 20 minutes. The cartridge is then drained.

Next, the RaMPS resin is soaked for 30–45 seconds with 100% DMF, drained and aspirated. This is repeated twice. (three cycles total)

A monitoring step is added at this point to detect incomplete deblocking reactions and to prevent human errors.

(If, at this point, the last amino acid has been coupled to the resin, cleavage of the completed peptide should be done next.)

RaMPS resin are then soaked for 30–45 sec with 100% methanol, drained and aspirated. This is repeated. (two cycles total)

RaMPS resin are soaked for 30–45 sec with 100% DMF, drained and aspirated. This is repeated three times. (four cycles total)

The next amino acid may then be added using the procedure outlined above, beginning with the first step.

After a length of 30 amino acids is reached, half of the resin is removed and placed in a separate cartridge. The concentration of amino acid is kept the same but the ratio of [AA/[Peptide chain on resin] is doubled].

Cleavage of the Completed Peptide

The RaMPS™ resin is soaked for 30–45 sec with 100% methanol, drained and aspirated. This is repeated twice. (3 cycles total).

The resin is aspirated for 10 minutes so that it will dry.

After the valve of the RaMPS cartridge is closed, the following is added: 2.85 ml trifluoroacetic acid (TFA); 135 ul phenol (H2O liquified) or thioanisole, as appropriate; 15 ul ethanedithiol.

The RaMPS cartridge is then capped and rocked at room temperature as noted.

| RapidAmide ™ resin | 16 hours |
|---|---|
| Wang resin | 3 hours |

Next, RaMPS cartridge is removed from the RaMPS processor and suspended over a 50-ml polypropylene tube.

The valve is opened, uncapped, and the solvent is drained into the tube.

The resin is next rinsed with 5.0 ml TFA, and drained into the tube. This is repeated.

The RaMPS cartridge may then be discarded.

The volume of TFA may then be reduced to 1–2 ml with a gentle stream of inert gas.

Next, 25 ml diethyl ether is added to the tube and mixed. The tube is then set on dry ice/acetone for 5 minutes or until the peptide precipitates.

The top ether layer may be removed and discard.

The previous two steps are to be repeated three times. (four cycles total)

Next, 25 ml ethyl acetate/diethyl ether (1.5:1) is added to the tube, and mixed. The tube is then set on dry ice/acetone for 5 minutes or until the peptide settles.

The top ether layer may be removed and discard.

The previous two steps are to be repeated. (two cycles total)

Next, 1.0 ml H$_2$O and 25 ml diethyl ether are added to the tube. The tube is then set on ice 5 minutes or until the layers separate. The top ether layer is discarded.

Any remaining ether is evaporated with gentle stream of inert gas.

The peptide may then be lyophilized from H$_2$O or put in a Speed-Vac.

The method of the present invention represents a breakthrough in the routine production of synthetic peptides of lengths 60 to 105 amino acids and greater, as long as native conformation structure in the absence of glycosylation is maintained. Typically, the efficiency of peptide synthesis decreases by 5% for each amino acid coupling past 20. (Grant, G. A., Evaluation of the Finished Product, in "Synthetic Peptides, A User's Guide" (1992), G. A. Grant eds., W. H. Freeman and Company, New York, pp. 185–258.) Therefore, with 5% error/per coupling, attempting to produce a peptide having 40 amino acids would result in none of the desired product.

Currently, the most common method to increase the efficiency for the production of longer peptides (for instance, peptides of 40 to 60 amino acids in length) is to perform two couplings of the same amino acid sequentially. Unfortunately, this results in increases the error at a given step and the frequency of certain side reactions with difficult amino acid couplings. Consequently, the inventors were quite surprised at the efficiency with which they were able to produce mucin to 105 amino acids. The longest peptide previously produced by Fmoc synthesis was 86 amino acids. (Field et al., Principles and Practice of Solid-Phase Peptide Synthesis,"in "Synthetic Peptides, A User's Guide" (1992), G. A. Grant, eds., W. H. Freeman and Company, New York, pp. 77–183.) In order for this to be accomplished, the fidelity of each step in synthesis had to be close to 100%. This can be achieved with engineered sequences as long as the proline content is relatively high (for instance, 15% or greater).

In another embodiment, the present invention relates to a method of producing mucin-like peptides having at least two tandem repeats and a foreign amino acid sequence, which mucin-like peptide is capable of attaining native conformation in the absence of glycosylation. The method relates to standard solid state synthesis protocols, with several modifications.

Conventional methodology is employed with the following modifications. Synthesis is stopped when the primary sequence reaches 30 amino acids in length. One half of the resin-bound 30 amino acid peptide is then removed. A monitoring step is then employed to monitor the completeness of the reaction. Then, the reaction cycle is continued until the desired length of peptide is obtained.

The method comprises the steps of:

i) activating an amino acid of interest;

ii) introducing the activated amino acid of interest to appropriate solid phase;

iii) reacting under appropriate conditions until completion;

iv) monitoring for completeness of reaction;

v) repeating steps i) to iv) with the next amino acid of interest, until a 30 amino acid peptide is obtained, at which point half of the 30 amino acid peptide is removed; and vi) continuing the reaction cycle until a mucin peptide of desired length having at least two tandem repeats and a foreign amino acid sequence, and is capable of attaining native conformation in the absence of glycosylation is formed.

By way of example, the above-described protocol may be employed to achieve the present invention.

The foreign amino acid sequence may be an epitope, such as, for instance an antigenic epitope corresponding to a virus (for example, HIV), a bacteria, or cancer (for example, pancreatic cancer, breast cancer, ovarian cancer or colon cancer). (Baehr et al., (1989) Mol. Microbiol. 3: 49–55) Epitopes which can be incorporated into the multiple tandem repeat synthetic peptide are shown in Table 2.

For example, T cell epitopes would be quite short, often only 3–4 amino acids in length. B-cell epitopes, on the other hand, are typically longer, although some can be as short as 3–5 amino acids.

The invention also relates to the mucin peptides produced by the above-described methods, which peptides may be 40, 60, 80 or, preferably, 105 amino acids in length, although longer lengths are possible as long as the secondary structure is not disrupted.

In addition, the invention presents practical methodology for producing a class of synthetic peptides that contain important antigens for vaccine and diagnostic development for human cancers and infectious diseases (Finn, Biotherapy 4: 239–249 (1992)). The poly-proline helix offers a potential framework structure for designing new antigens by tandemly repeating important B- or T-cell epitopes or coupling of B- and T-cell epitopes to produce antigens of larger sizes.

Thus, in another embodiment, the present invention relates to an immunogenic composition or molecule capable of inducing in a mammal antibodies against an epitope (such as a vaccine), which composition or molecule comprises a synthetic muc-1-like peptide. The synthetic muc-1-like peptide comprises at least two 20-amino acid tandem repeats of muc-1 and the amino acid sequence for the epitope, and the synthetic muc-1-like peptide is capable of attaining native conformation in the absence of glycosylation. The synthetic muc-1-like peptide may comprise 2, 3, 4, 5 or more muc-1 tandem repeats, and may be 40, 60, 80 or, preferably, 105 amino acids in length, although longer lengths are possible. The immunogenic molecule can be administered with an adjuvant.

Mucin tandem repeat polypeptide core region is immunogenic and HLA-unrestricted because it has a secondary structure rich in prolines, which is stable, assumes native configuration, is a structural, not only a sequence repeat, and due to all of this is capable of direct binding and cross-linking of T cell and B cell antigen receptors. For instance, by the methods of the present invention, a synthetic peptide may be produced, 105 amino acids in length, containing 5 tandem repeats of 20 amino acids in length each, and five amino acids (such as, for instance, GVTSA, which may be placed on the back end or, preferably, the front end of the peptide). The longest mucin synthetic peptide reported to date has two repeats; more than two tandem repeats are critical for the peptide to assume a native structure and thus react properly with antibodies, to induce proper antibodies, and to stimulate cellular immunity.

This method of synthesis which is especially effective for peptides with characteristically placed prolines. Furthermore, the present invention can be utilized for synthesis of other very long peptides in which a particular short sequence can be synthesized on a long mucin-like backbone which can give the peptides a more native configuration and desired reactivity with antibodies or cells of the immune system. The synthesis of complex peptides using a polyproline β-turn helix structural motif constitutes a novel synthetic strategy that can produce remarkably high levels of efficiency and precision in the synthesis of exceedingly large peptides (for instance, longer than 40 amino acids).

The 105 amino acid long synthetic mucin peptide can be used as a tumor specific vaccine for patients with pancreatic, breast, ovarian and colon cancers. Previous studies have shown that epitopes on the mucin polypeptide core are targets for tumor specific cytotoxic T cells, and that their immunogenicity depends on several of them being tandemly repeated. These epitopes are present on the 105 amino acid synthetic peptide and tandemly repeated 5 times. Immunization of mice with this peptide in soluble form and with incomplete Freunds adjuvant generates a desired cellular immunity. This has not been achieved previously with short synthetic peptides. The length of the peptide which allows for the native structure to form, and the tandemly repeating epitopes are novel characteristics of this molecule and may be responsible for its immunogenicity.

Although the cDNA sequence of the mucin gene was available, the use of a tandemly repeated epitope for MHC-unrestricted stimulation of the immune response was not predictable. It is a novel discovery that a structurally stable, tandemly repeated molecule, which contains important immunogenic amino acid residues derived from any antigen (bacterial, viral, tumor, autoantigen) will be capable of eliciting an immune response in all individuals, independent of their HLA (MHC) molecules. Furthermore, the technique for successfully synthesizing these long tandem repeat peptides is novel as well.

The mucin structure may be used as the prototype of such a structure. An example is shown below:

| MUCIN (SEQ ID NO: 1) |
|---|
| A P D T R P A P G S T A P P A H G V T S A P D T R P<br>A P G S T A P P A G G V T S |
| A HYPOTHETICAL IMMUNOGEN (SEQ ID NO: 2) |
| (e.g. viral epitope, bacterial epitope, autoantigen) |
| X P X X X P X P G S T A P P A G G V T S A P X X X P<br>X P G S T A P P A G G V T S |

The multiple prolines are necessary for maintaining the rigid structure, even though their exact position may not have to be maintained. The sequence DTR in the mucin, located between the first two prolines in each repeat, is the target of the anti-mucin immune response. The rest of the sequence is inert for purposes of an immune response and can be left unchanged to serve as scaffolding, which further maintains the three dimensional structure. The DTR sequence can be substituted by a sequence from a virus, tumor antigen or autoantigen.

In general, the substitution sequence is a short peptide (for instance, about 3 amino acids long), in which only two or three amino acids are capable of contacting a T cell receptor for recognition by the immune system. The short peptide may, for instance, be derived from a long peptide bound to HLA.

Because most of these short amino acid sequences do not have a stable structure, they must bind to an HLA molecule in order to be presented to the immune system. This binding is very specific and depends on a specific type (allele) of an HLA molecule. Thus when an immunogenic sequence is identified by its ability to stimulate immune response in some individuals, there will be other individuals with different HLA types such that their immune system will not be stimulated by it. This dependence on HLA is known as HLA restriction and it is a problem which must be overcome in designing peptide-based vaccines. The mucin-like structure bypasses HLA-restriction and the need for peptide presentation by providing the necessary rigid, stable, and tandemly repeated structure capable of activating T cell receptors, B cell receptors and the immune system.

Multiple tandemly repeated mucin epitopes stimulate T-cells directly, independent of presentation by patients' HLA molecules. The long synthetic mucin peptide containing 5 or more tandem repeats is designed to stimulate T cells directly. This is very significant, as peptide vaccines are usually restricted in use by the HLA type of a patient and its ability or inability to present the vaccine peptide. The long synthetic mucin peptide can be used as a vaccine in all patients. Furthermore, any immunogenic sequence superimposed on the mucin-like structure may be capable of stimulating an immune response in all subjects regardless of the HLA type.

The principles established with the long synthetic mucin peptide regarding the ability of tandemly repeated epitopes to stimulate immune responses independently of patients' HLA types, can be applied to other epitopes found in tumor antigens, in viral antigens, and in autoantigens. These epitopes are immunogenic only in a sub population of people with a particular HLA type capable of presenting them. Synthesizing these epitopes according to the mucin structure may render them independent of presentation by HLA molecules, and immunogenic in all individuals. Thus, one advantage of using the peptides of the present invention is their ability to induce a non-MHC-restricted immunogenic response in mammals regardless of their HLA type.

For instance, synthetic mucin peptide composed of five tandem repeats and 5 amino acids (such as, for instance, GVTSA, which may be placed on the back end or, preferably, the front end of the peptide), 105 amino acids long, may substitute for the native molecule as an immunogen. Thus, it is ideal for use as a synthetic vaccine. Synthetic mucin 105 peptide represents a prototype of a stable tandem repeat structure, onto which other immunogenic epitopes can be synthesized, and immune responses to them made HLA-unrestricted.

These immunogenic conjugates would be suitable for immunization against the disease whose antigenic epitope has been designed into the multiple tandem repeat synthetic peptide when administered in an immunogenically effective amount to a mammal, for example by the intradermal route.

Epitopes which can be incorporated into the multiple tandem repeat synthetic peptide include, for instance, an antigenic epitope corresponding to a virus (for example, HIV), a bacteria, or cancer (for example, pancreatic cancer, breast cancer, ovarian cancer or colon cancer). (See Table 2.)

In a further embodiment, the present invention relates to a method of inhibiting an immune response in a mammal, comprising the step of administering the above-described mucin-like peptide composition to a mammal in an immunogenically effective amount, which epitope is recognized by an autoantibody produced by the mammal. The mucin-like peptide will be recognized by the antibody and prevent its binding to the native target.

Vaccines of the instant invention, which, when administered to a mammal, induce a protective immunogenic response against the epitope present on the repeats, comprise one or more immunogenic mucin-like peptide, comprising a peptide with the disease-specific epitope, wherein each disease-specific epitope corresponds to a different portion of the epitope.

In addition, it is possible to produce a bivalent vaccine whereby immunogenic peptides described above, comprising synthetic peptides from epitopes of two different diseases, are mixed to form a single inoculum such that protective antibodies will be simultaneously raised in a mammal to both diseases.

As discussed above, the synthetic method of the invention is novel in that it achieves efficient and reliable synthesis of long peptides. There are a number of advantages associated with peptides of long length over the shorter peptides currently being synthesized. These advantages include, for instance, (1) the formation of native structure, (2) the inclusion of more sequence and structural information within the same molecule, (3) the fact that larger peptides make better antigens, (4) the ability to cross link the antigen receptors of both B and T antigen receptors on the surface of immune system cells and directly induce either antibody production or T cell activation, and (5) the development of high avidity type interactions between a given peptide substrate and multivalent antibodies (for diagnostic purposes).

With respect to the formation of native structure, the poly-reverse turn structure of this peptide motif may enable the use of the peptide for the development of vaccines. For a folded native protein, the backbone, which is composed of the linear sequence of amino acids, the chain traverses the hydrophobic interior of the protein and turns around at the surface using a reverse turn (or β-turn) to reverse the direction of the protein chain. The important antigens of bacteria and viruses are proteins and fold the same way, so a large portion of the surface of an antigen is composed of these turns.

Consequently, during an infection, antibody molecules, which are on the surface of B cells, first come into contact with the surface viral antigens, in their native fold, which are reverse turns. Turn structures are the easiest types of secondary structure to predict or to detect based on the sequence alone, without actually solving the structure of the protein. These structures are typified by the presence of proline and glycine. Many of the known neutralizing (protective) antibody binding sites of many viral and bacterial antigens are known or are believed to be these turn structures.

For example, the primary neutralizing determinant of HIV-1(the V3 loop), the virus that causes AIDS, contains the essential sequence GPGRAF. By all criteria of protein secondary structure prediction and by experimental determination, this sequence forms a reverse turn in the native protein. Antibodies to this structure are known to neutralize HIV-1 and hence protect from the pathogenic effects of the virus. This sequence can be substituted into the mucin sequence in the following way:

| | |
|---|---|
| MUCIN | P D T R P A P S T A P P A G G V T S A |
| HIV-MUCIN | G P G R A F P A P S T A P P A H G V T S A |
| OR | P D T R P A P S T A P P A G P G R A F |

(see SEQ ID NOS: 3, 4 and 5, respectively)

The synthetic production of these sequences in a repeating manner will produce a mucin-like molecule with multiple copies of the V3 loop in what may be the native turn structure. This peptide molecule may be used beneficially, such as in the following applications.

It has been shown that mucin-like molecules can induce IgM antibodies. IgM antibodies are pentavalent (5 copies joined together in a cylindrical manner) and therefore quite large. Thus, these antibodies may be excellent neutralizing antibodies. The huge size may be very effective in blocking the entry of the virus into the cell. Currently, none of the known neutralizing antibodies to HIV-1 are IgM, because only polyvalent antigens induce IgM.

Furthermore, IgM can be induced independently of T cells in an HLA unrestricted fashion. This would be advantageous to AIDS patients who are T-cell depleted and/or T-cell suppressed and are, therefore, unable to mount effective HLA restricted immune responses. A large poly-valent V3 loop antigen could be a very effective immunotherapeutic agent for HIV-positive people, and could significantly boost the immunity to the virus and slow or prevent the onset of AIDS in these hopeless people.

Longer peptides are also advantageous in that more sequence and structural information within the same molecule are included. For instance, additional sequences that code for T-cell epitopes could be inserted into the proline rich backbone and tandemly repeated to produce a mucin like molecule to induce antibodies in a T-cell dependent fashion or HLA-restricted fashion.

In addition, longer peptides make better antigens than shorter peptides. Furthermore, longer peptides exhibit the ability to cross link the antigen receptors of both B- and T-antigen receptors on the surface of immune system cells, and directly induce either antibody production or T-cell activation. Also, longer peptides would enable the development of avidity type interactions between a given peptide substrate and multivalent antibodies, which is useful in, for instance, diagnostic testing.

In addition to the use of these peptides as a vaccine, or as a component of a vaccine, the peptides of the present invention can also be used for diagnostic purposes. The presence and titers of antibodies to a specific disease in biological samples can be detected using synthetic peptides designed with the specific epitope for an immunogenic agent of the disease being measured.

Thus, in yet a further embodiment, the invention relates to a method of detecting the presence of antibodies to a specific disease (for instance, cancer, HIV, autoantibodies) in a biological test sample, comprising the steps of:

a) contacting the above-described synthetic muc-1 or muc-1-like peptide containing an epitope with the biological test sample (such as, for instance, serum or plasma), which epitope is reactive with antibodies to the disease, under conditions such that a synthetic muc-1 or muc-1-like peptide-antibody complex is formed, and b) detecting the formation of the synthetic muc-1 or muc-1-like peptide-antibody complex, which complex is indicative of the presence of antibodies to the specific disease. These peptides can be used, for example, in a standard enzyme-linked immunosorbant assay (ELISA) or an radioimmuno assay (RIA) to detect the presence of antibody in biological samples.

In addition, the peptides may be used as a diagnostic reagent to evaluate patients' immune responses to their tumors pre and post immunization. For example, long synthetic mucin peptide may be a useful indicator of an ongoing immune response in patients with pancreatic, breast, ovarian, and colon cancers. The presence of anti-mucin antibody, before and after immunization cannot be detected with short peptides, but is easily detectable when, for instance, the 105 amino acid peptide is used in ELISA. This peptide may be useful even in unimmunized patients for measuring the low level but existing immune response to the tumor. Thus, the peptide may be used for distinguishing between patients who are already responding to their tumor, and those who are not, which may significantly influence any decision regarding the course of treatment and prognosis of the patient's disease.

In view of the foregoing and the state of the art, it will be clear to those of ordinary skill in the art that disease specific test kits can be constructed for detecting antibodies to the desired disease in biological samples using techniques for detection that include ELISA, RIA, indirect immunofluorescence and Western blot analysis.

In another embodiment, the invention relates to a method for inhibiting the growth of cancer cells. The method comprises the steps of:

a) obtaining antibodies to the tumor cells by injecting a test mammal using conventional techniques (for example, a mouse or a rabbit) with the above-described synthetic muc-1-like peptide containing an epitope, which epitope is reactive with antibodies to the cancer cells, under conditions such that a synthetic muc-1-like peptide-antibody complex is formed, and isolating said antibodies from the complex from the mammal, b) contacting the isolated antibodies from step a) with an agent capable of inhibiting the growth of cancer cells, under such conditions that an antibody-agent complex is formed, and c) contacting the antibody-agent complex from step b) with cancer cells, under such conditions that the antibody-agent complex reacts with cancer cells and inhibits the growth of the cancer cells.

The agent may be a radioisotope (for example, Yttrium 90 and Iodine 131), chemical (for example, methotrexate), toxin (for example, ricin or parts thereof), or enzyme.

The invention also relates to methods of inhibiting or blocking an immune response in a mammal. One and two tandem repeats, (i.e., 20 or 40 amino acids) maintain stable secondary structure and react well with specific monoclonal antibodies. In general, to stimulate the production of antibodies, peptides having several tandem repeats which can cross-link antigen receptors are required. However, since the shorter form maintains stable structure but is incapable of cross-linking receptors and activating the immune system, it may be used for blocking immune responses. This may be very important in autoimmunity and in transplantation.

Thus, in another embodiment, the invention relates to a method of inhibiting an immune response in a mammal, comprising the step of administering the above-described immunogenic composition to a mammal in an immunogenically effective amount, wherein the epitope is recognized by an autoantibody produced by said mammal.

Synthetic mucin tandem repeat peptides of only 20 or 40 amino acids do not stimulate immune responses because they cannot cross-link receptors. However, for purposes of inhibiting or blocking immune responses, various antigens or targets of an undesired immune response can be synthesized onto the mucin structure and used to block the interaction of the immune response with its natural target.

Target antigens in autoimmunity are not known yet. However, techniques now exist to begin to identify specific peptides involved in autoimmune responses. When these peptides are identified, two- or three-amino acid residues will also be identified that are specifically recognized by autoimmune T cells. These residues may be used to replace DTR or some other amino acids in the mucin short tandem repeat peptide. Because this peptide would be mucin-like, and thus structurally stable, it is expected to bind directly to the T cell and B cell receptors and antibodies and block their interaction with the target antigen.

An example of an autoimmune disease where this blocking strategy may be applied is rheumatoid arthritis. Even though the target antigen is not known, there is a very strong association of rheumatoid arthritis and the presence of HLA-Class II molecules which share all of the amino acid sequences, three amino acids long. These sequences are thought to be involved in presenting the antigen to T cells. By substituting the mucin DTR sequence by one of these amino acid sequences on a short synthetic tandem repeat peptide (20 or 40 amino acids) it may be possible to block autoimmune T cells.

All autoimmune diseases are characterized by the presence of autoantibodies. In many instances the precise targets of these antibodies are known. These antibodies could be prevented from binding to their targets with short mucin peptides carrying specific epitopes recognized by the antibodies.

In the present invention, long tandem repeat peptides (for example, 105 amino acids in length) are stimulatory because they not only bind but also cross-link receptors. Short (for example, 20 or 40 amino acids in length) are expected to block or inhibit an immune response because they bind but do not cross-link. In that way they can only interfere with binding to the real target.

The target antigen in graft rejection is the HLA molecule itself. It may be possible to use sequences which differ between the organ donor and the organ recipient HLA, synthesize them on the mucin structure and use to block cells or antibodies rejecting a transplanted organ.

The following non-limiting examples illustrate the invention in more detail:

EXAMPLES

The following materials, methods and protocols were used in the examples below.

Peptide Synthesis

Peptides were synthesized using manual methods on a Rapid Multiple Peptide Synthesizer (RaMPS) purchased from Dupont (Boston, Mass.). The syntheses were performed using 0.1 mM Rapid Amide (2,3-dimethoxybenzhydrylamine) resin cartridges purchased from Dupont (Boston, Mass.). The solvents N,N-dimethyl formamide (DMF) protein sequencing grade, methylene chloride (DCM) certified A.C.S. grade, and methanol Karl Fischer grade were purchased from Fischer Scientific (Fair Lawn, N.J.). The deprotection reagents of anhydrous piperidine and trifluoroacetic acid protein sequencing grade, were purchased Sigma (St. Louis, Mo.). The scavengers 1,2-ethanedithiol, thioanisole, and anisole were purchased from Dupont (Boston, Mass.).

The Fmoc amino acid side chain protecting groups were tert-butyl esters (OtBu) for aspartic and glutamic acid; tert-butyl ethers for serine, threonine, and tyrosine; 2,2,5,7,8-pentamethylchroman-6-sulfonyl (Pmc) for arginine; tert-Butyloxycarbonyl (Boc) for lysine; triphenylmethyl (trt) for histidine; and all Fmoc amino acids were purchased from Advanced Chem Tech (Louisville, Ky.). The amino acids were coupled as symmetric anhydrides for alanine, arginine, and histidine; active esters of pentafluorophenol for asparagine, aspartic acid, glutamic acid, glutamine, glycine, isoleucine, leucine, lysine, methionine, phenylalanine, proline, tryptophan, tyrosine, and valine (OPfp); active esters of 3-hydroxy-2,3-dihydro-4-oxo-benzotriazine (ODhbt) for serine and threonine; active esters of 1-hydroxybenzotriazole (HOBt) for histidine. The coupling times were a standard one hour at room temperature using 0.25 mmol OPfp and ODhbt activated amino acids and 0.1 mmol of HOBt in three ml DMF. Coupling reactions using 0.25 mmol of HOBt or symmetric anhydride activated amino acids were performed in 2 ml DMF and 1 ml DCM for one hour at room temperature. The peptide resins were split in half after a chain length of 30 amino acids was reached but the concentration of input amino acid for the newly separated fractions was maintained at 0.25 mmol per 3 ml of solvent. Ninhydrin reactions were performed at the completion of each coupling reaction using ninhydrin test kit reagents purchased from Dupont (Boston, Mass.).

The Fmoc Nα protecting group is removed at the completion of a synthetic cycle by shaking for 20 minutes in 3 ml 50:50 piperidine:DMF, followed by extensive washing with DMF and methanol. The side chain protecting groups and cleavage of the peptides from the resins were performed by shaking in 3 ml of 90:5:3:2, TFA: thioanisole: 1,2-ethanedithiol: anisole for 4 hours at room temperature in 5 ml poly-propylene Quik-Sep disposable chromatography columns from Isolab (Ackron, Ohio). The TFA and peptide mixture was drained from the column into cold ethyl ether, followed by three sequential extractions with ethyl ether, three extractions with 60:40 ethyl ether:ethyl acetate. Finally, the peptide is extracted into 3 ml of water and lyophilized.

Peptide Purification

The crude peptide mixtures were purified by analytical reverse phase high pressure liquid chromatography (RP-HPLC) on a Waters 600E chromatograph, with a Waters 486 absorbance detector (Milford, Mass.) and a Linear 1200 series recorder from Cole Palmer (Chicago, Ill.). Analytical separations utilized a Delta Pak C18, 300 Å (3.9×300) mm RP-HPLC column and semi-preparative separations used a uBondaPak C18, (7.8×300) mm column from Waters (Milford, Ill.). Chromatography solvents were HPLC grade acetonitrile from Fisher Scientific (Fair Lawn, N.J.) and water both containing 0.1% TFA. The chromatographic separations were performed using a 1% per minute linear gradient of water (0.1% TFA) and acetonitrile (0.1% TFA). Initial conditions were 95:5. water:acetonitrile and final conditions were 40:60, water:acetonitrile.

Mass Spectrometry

Electrospray ionization mass spectra were obtained using a Vestec electrospray source and model 201 single quadruple mass spectrometer (Vestec Corp., Houston, Tex.) fitted with a 2000 m/z range (1,2). Samples were delivered to the source in a 10 microliter injection loop at 5 microliters/min in 4% acetic acid: 50% acetonitrile.

Circular Dichroism

The circular dichroism spectra were recorded on a Japan Spectroscopic Company (Jasco) model J-710 circular dichroism spectropolarimeter (Hachioji City, Japan). The temperature was controlled using a Jasco PTC-343 peltier-type thermostatic cell holder and temperature control program. The spectrum was recorded from 195–260 nm with readings every 0.1 nm at 25°, 55°, 75°, and 90° C. The peptide concentration was 0.1 mg/ml of HPLC purified peptide in 0.01 M phosphate buffer at pH 7.2 except for the peptide H2D8 which was used at 1.0 mg/ml in 20:80, acetonitrile:phosphate buffer (0.01M pH 7.2). A 0.1-cm path length strain free quartz cuvette was used to record the spectrum. The solvent spectrum was subtracted from that of sample and a noise reduction subroutine was applied to the resultant spectrum. A total of ten scans were accumulated for each sample. No change in the solvent spectrum was observed with increasing temperature.

$^1$H-NMR Spectroscopy of TR Peptides $^1$H-NMR analyses was performed using HPLC purified and lyophilized peptides. The concentrations used were from 6–7.5 mM in 0.1M phosphate buffer, pH 5.9 with either $H_2O/D_2O$ (90%/10%) or $D_2O$ (99.9%). We chose to use a high ionic strength buffer to reduce the electrostatic interactions between molecules. A pH of 5.9 was chosen for the $D_2O$ studies to avoid perturbations of the spectra resulting from the partial protonation of histidine, but significantly different from the pKa value of histidine. The 1-dimensional $^1$H-NMR experiments in $H_2O$ were performed at pH 6.8.

A Bruker AM-500 NMR spectrometer equipped with Aspect 3000 computer and a 5-mm $^1$H probe was used to record the spectra of the mucin muc-1 peptides. The spectra were recorded at 25° C., with the temperature of the probe regulated with a BVT-1000 unit and calibrated with a methanol sample. The $D_2O$ spectra of the peptides were recorded 5 to 10 minutes after dissolution. Suppression of the water signal was accomplished during the repetition delay of 1.5 seconds for peptide samples in $D_2O$ and $H_2O$. The one-dimensional spectra were recorded following a single 90° pulse. A control spectrum of the $H_2O$ sample was taken without water presaturation to ensure that none of the amide protons were affected by presaturation of water signal at any given power level. A total of 1024 transients were collected for each spectrum. The two-dimensional correlated spectra (COSY) was recorded in a phase sensitive mode. A sine bell filter was applied to the time domain data in both F1 and F2. The acquired data size was 2048×1024 points. Zero filling was used to obtained a final data matrix of 4096×4096 points. All proton chemical shifts were relative to the reference compound 2,2-dimethyl-2-silapentane-5-sulfonate (DSS) at 0.0 ppm.

Intrinsic Viscosity

All viscometry measurements were performed using a Cannon-Fenske-Ostwald type capillary viscometer with HPLC purified peptide in 0.1M phosphate buffer at pH 7.0 and 30° C. The procedure was as described previously (Tanford, et al., J. Am. Chem., 89: 729–736, 1967 and Buzzell, et al., J. Phys. Chem. 60: 1204–1207, 1956). The capillary constant was as calculated as reported by Tanford and Buzzell, 1956 (Tanford, et al., J. Phys. Chem. 60: 225–231, 1956). The kinematic viscosity measurements were repeated at least ten times, and the averages were used to calculate the intrinsic viscosity. Intrinsic viscosity was calculated from kinematic viscosity, and the appropriate density correction (0.0029 ml/g) was applied as recommended (Tanford, 1955). The Simha shape factor and the peptide axial ratios were calculated according to (Tanford, 1961 and Cantor, et al., 1980).

Molecular Modeling of the 60 Amino Acid Peptide

The sequence of the tandem repeat (TR) domain of the human mucin muc-1 (Gendler, et al., PNAS USA, 84: 6060–6054, 1987) gene was modeled into a polytype I turn conformation on a silicon graphics model INDIGO (Mountain View, Calif.) terminal using the Tripos molecular graphics program SYBYL (St. Louis, Mo.). Using this model the longitudinal axis and cross sectional axis were measured, and the axial ratio (longitudinal/cross sectional) of the 60 amino acid peptide was estimated (Table III).

The TR domains of human mucins muc-1,2,3,4 were also modeled according to the rules of Chou and Fasman (1978) (Chou, et al., Ann. Rev. Bioch., 47: 251–276, 1978) for secondary structure prediction. Surface potential was predicted using the "Surface Plot" algorithm as described (Parker, et al., Biochemistry, 25: 5425–5431, 1986). Potential amphipathic alpha-helical regions were predicted using the "Amphi" algorithm of Margalit et al. (Margalit, et al., J. Immunol., 138: 2213–2229, 1987). The results of these analyses were used to construct conformational models (results not shown). The number of predicted turns per repeat is summarized in Table I.

EXAMPLE 1

Peptide Synthesis

Sequences of peptides which were synthesized by RaMPS are shown in table 4. The naturally occurring mucin tandem repeat is shown in table 4, number 1. The entire proline rich neutralization domain of Feline leukemia virus and a 42 amino acid N-terminal fragment of this domain is shown in table 4, No. 2, and 3, respectively. The T-cell epitopes that were used to construct the engineered tandem repeat proteins and shown in table 4, No. 4, and 5 respectively.

Figure 8H:
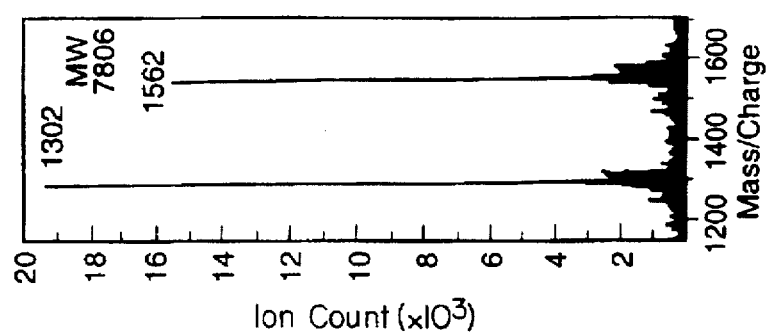
Figure 8G:
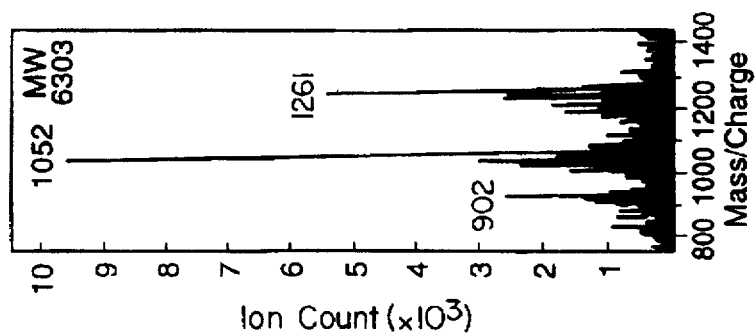
Figure 8F:
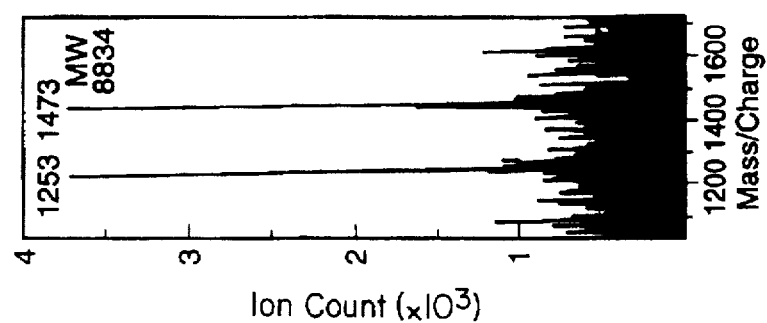
Figure 8E:
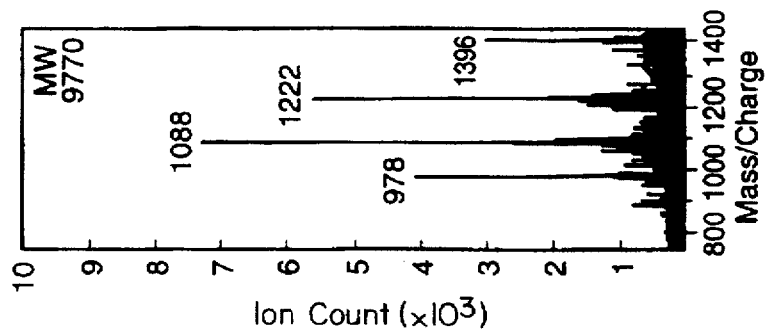

Using the human mucin muc-1 tandem repeat sequence as indicated in Table 4 we synthesized a series of peptides consisting of 1, 2, 3, 4, and 5.25 complete tandem repeats by manual solid phase peptide synthesis as described above. FIG. 8a shows the HPLC profile of the crude peptide products from the synthesis of the 105 amino acid mucin peptide. The electrospray mass spectrum (EMS) of the major fraction showing the correct molecular weight of 9770 daltons is shown below (FIG. 8e). The HPLC profile obtained with the 105 amino acid mucin peptide and the EMS are representative of the profiles from the syntheses of the 20, 40, 60, and 80 acid peptides corresponding to 1,2, 3, and 4 tandem repeats of the human mucin muc-1 protein core. They all exhibited extraordinary efficiency and fidelity of synthesis. The expected molecular weight was obtained for each of the mucin peptide syntheses as shown in Table 5. Upon semi-preparative purification of the mucin peptides 85–92% recovery final product were typically obtained.

The synthesis of the entire 60 amino acid proline-rich domain of the feline leukemia virus external surface unit gp-70E (FeLV-PRN60) was also attempted by RaMPS. FIG. 8b shows the analytical HPLC profile of the crude synthetic products from this manual synthesis. The EMS of the major fraction (FIG. 8f) and Table 5 shows that the correct molecular weight was obtained. A related peptide (PRN42) corresponding to the N-terminal 42 amino acids of PRN60 (see Table 4) was also synthesized correctly as indicated by the molecular weight of the major fraction (Table 5). All other peptides that correspond to smaller analogs of PRN60 were synthesized with equal efficiency and fidelity.

Next was synthesized a peptide corresponding to a tandemly repeated nine amino acid T-cell epitope from the cytomegalovirus pp89 sequence early regulatory protein (H2D8) shown in Table 4. This peptide was previously identified as the optimal immunogenic CTL epitope in H-2D$^d$ mice (Reddehase, et al. Nature, 337: 651–653, 1992; Boyd, et al., PNAs USA, 89: 2242–2246, 1992). This peptide was selected because it contains two proline separated by three amino acids as found in the major immunodominant B and T cell epitope (PDTRP) of the mucin tandem repeat (Barnd et al., PNAS USA, 86: 7159–7163, 1989; Jerome et al., Cancer Res. 51: 2908–2916, 1991). This peptide contains two proline residues per nine amino acids and is 22% proline. The HPLC profile of the crude synthetic 72 amino acid (H2D8) peptide containing eight tandem repeats is shown in FIG. 8c. The H2D8 peptide differs greatly from the mucin and FeLV peptides in hydrophobicity. The EMS results of the major HPLC fraction demonstrate that the correct peptide was obtained (FIG. 8g). A peptide corresponding to 5 tandem repeats showed similar results (Table 5).

In order to reduce the hydrophobicity of H2D8 a serine was added to position 10 in the sequence and phenylalanine 4 was substituted to alanine to create H2Dmuc7. This peptide was synthesized through seven tandem repeats (Table 4). These modifications in H2Dmuc7 were shown to result in a peptide with markedly reduced hydrophobicity as demonstrated by the HPLC profile of the 70 amino acid (FIG. 8d). The EMS spectra of the primary fraction shows that the correct peptide was obtained (FIG. 8h).

Figure 9A:
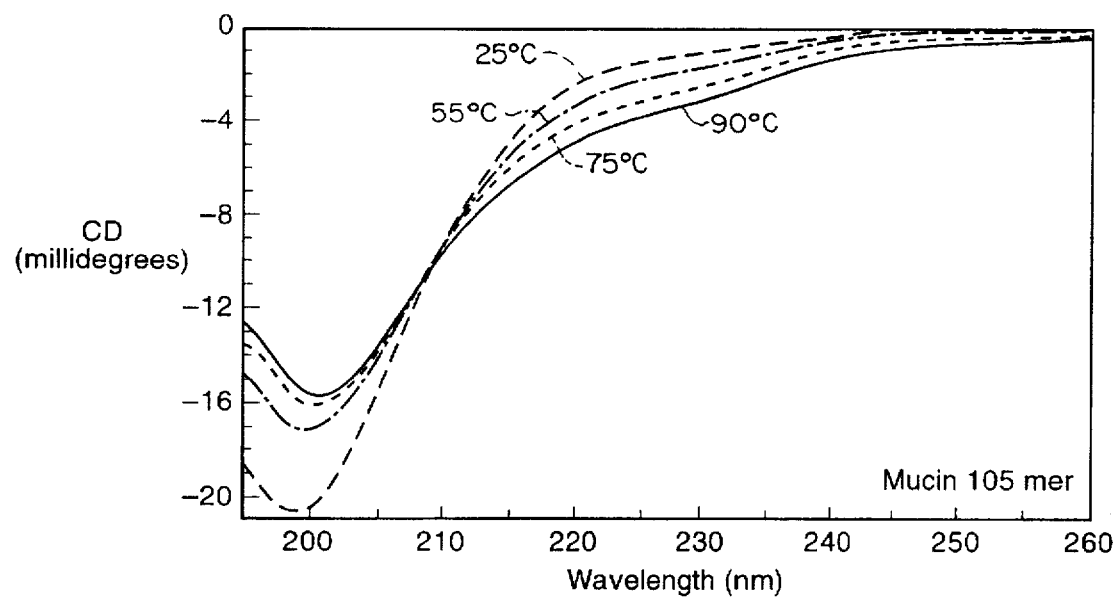
FIGS. 9A–D. Circular dichroism spectra of (a) mucin 105, (b) PRN60, (c) H2D8, (d) H2DAS7 at 25°, 55°, 75° and 90° C.
Figure 9B:
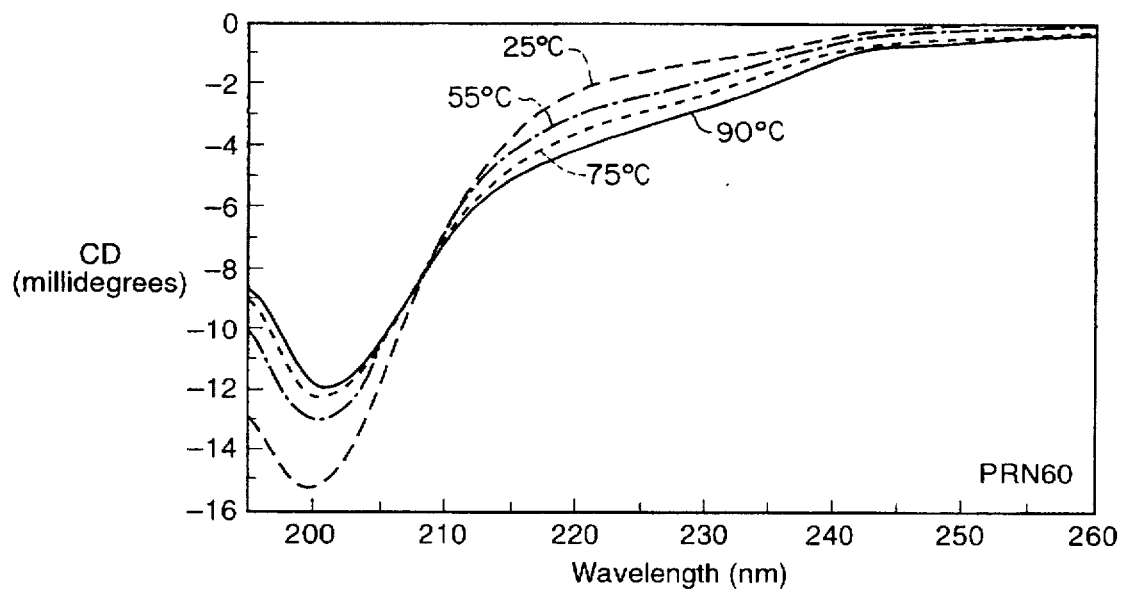
Figure 9C:
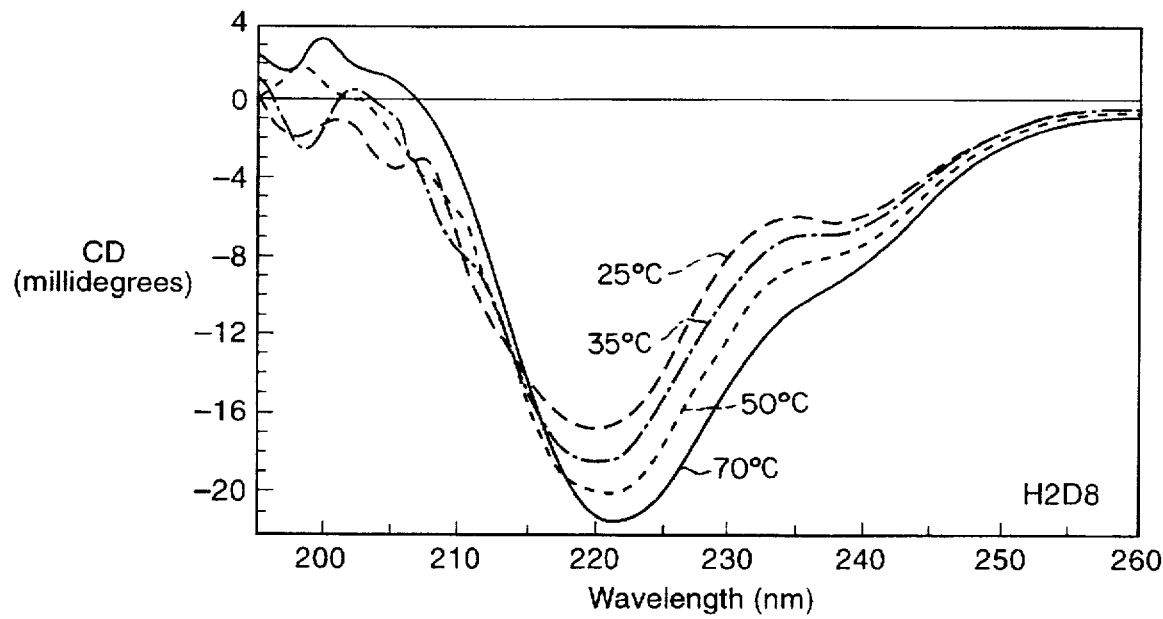
Figure 9D:
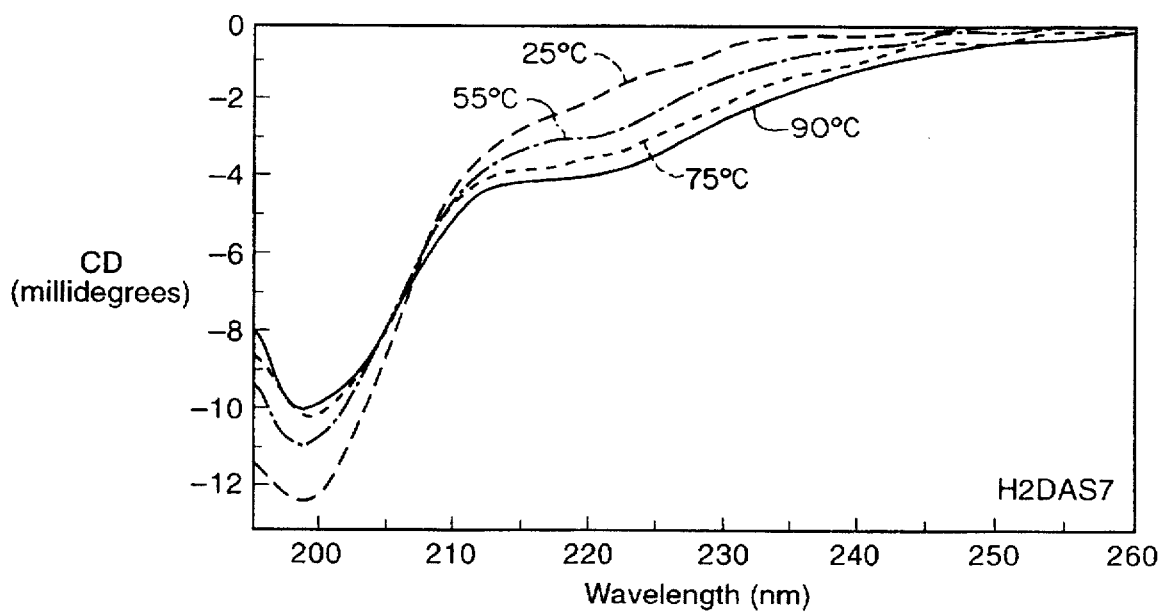

To investigate the possibility that the resulting peptide conformation can be correlated with the ease of synthesis, circular dichroism spectroscopy was performed on the HPLC purified peptides. The CD spectrum of the mucin 105 amino acid peptide is shown in FIG. 9a. The large negative peak at 198 nm is characteristic of proline rich proteins known to form extended structures including bovine elastin (Urry, J. Prot. Chem., 7: 1–34, 1987), C hordein (Tatham et al., Biochem. J., 226: 557–562, 1985), and collagen and poly-proline II (Madison and Schellman, Biopolymers, 9: 511–567, 1970b). The spectrum observed with feline leukemia virus PRN60 (FIG. 9b) is identical with that obtained for mucin. Due to hydrophobicity (H2D8) was not soluble in 0.01M phosphate buffer at pH 7.2 and the spectrum of the tandemly repeated T-cell epitope peptide was acquired in 20:80, acetonitrile: phosphate buffer. The spectrum consists of a large negative peak at 222 nm and a smaller negative band at 238 nm. The CD spectrum of the modified H2D8 peptide (H2Dmuc7) was acquired in phosphate buffer and is shown in FIG. 9d. This spectrum is similar to that obtained for mucin and PRN60 with a large negative CD band at 198 nm.

The large negative CD band at 198 nm is identical with that obtained for the model proline compound N-acetyl-L-proline-N,N-dimethylamide (AcProDMA) (Madison and Schellman, Biopolymers, 9: 511–588, 1970 b & c). The large negative CD band at 198 nm for AcProDMA in aqueous solution was shown to be due to three π-π* transitions and a large n-π* transition in the tertiary amide and was shown to be characteristic of proline in the trans conformation (Madison and Schellman, Biopolymer, 9: 511–588, 1970 b & c). The CD spectrum of AcProDMA in the cis conformation is favored in hydrophobic environments and results in a positive band at 198 nm and the resultant spectrum of a mixture of cis and trans isomers could be represented by a linear combination of the two spectra (Madison and Schellman, Biopolymers, 9: 65–94, 511–567, 1970 a & b).

To see whether the negative CD band at 198 nm is due to cis and trans proline isomers or conformational effects, the inventors tested the possibility that increasing the temperature would decrease the CD intensity at 198 nm. The CD spectra were recorded at 25°, 55°, 75°, and 90° C. FIG. 8a, b, and d show that the CD intensity at 198 nm in 0.01M phosphate buffer at pH7.2 was decreased at 90° C. as compared to 25° C. by 33% for mucin 105, 29% for PRN60, and by 22% for H2Dmuc7. In contrast, the CD intensity of the shoulder region from 215 to about 240 nm increases for all the peptides with increasing temperature. The set of temperature curves for mucin, PRN60, and H2Dmuc7 exhibit isocircular dichroic points at 208, 209, and 207 nm (FIG. 9a, b, and d). This suggests the existence of two discreet populations, one at high and one at low temperatures (Tatham et al., Biochem. J., 226: 557–562, 1984). The CD spectrum of H2D8 (FIG. 9c) was recorded at 10 fold higher concentration and was devoid of the large negative peak at 198 nm. This suggests that in 20% acetonitrile this peptide contains proline in the cis conformation. The remainder of the spectrum of H2D8 from behaved like the shoulder region of mucin, PRN60 and H2Dmuc7 with increasing temperature.

Figure 10:
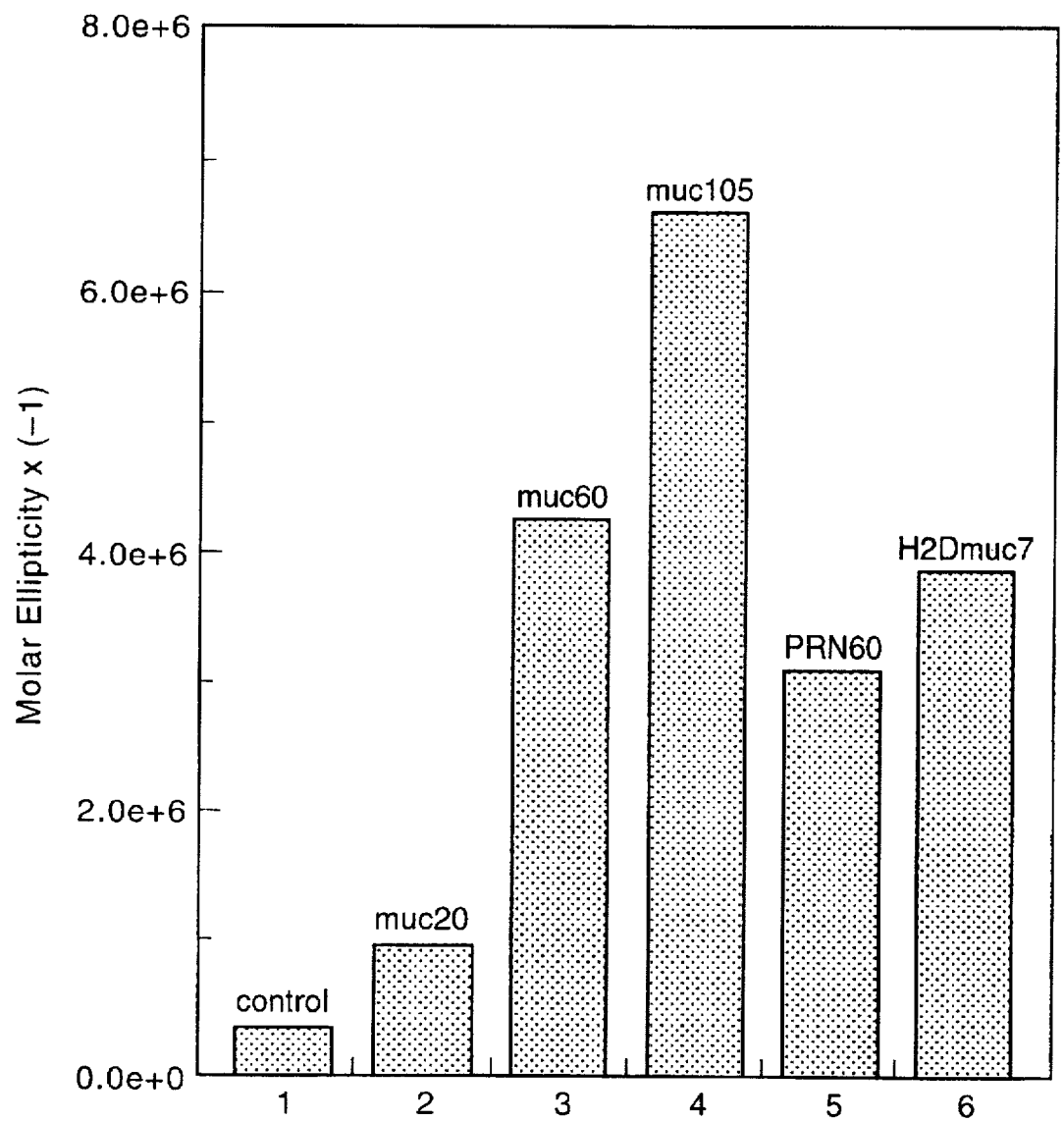
FIG. 10. The molar ellipticity [Θ] of (1) control peptide (2) mucin 20 residues (3) mucin 60 residues (4) mucin 105 residues, (5) PRN60, (6) H2DAS7 at 25° C.
Figure 11:
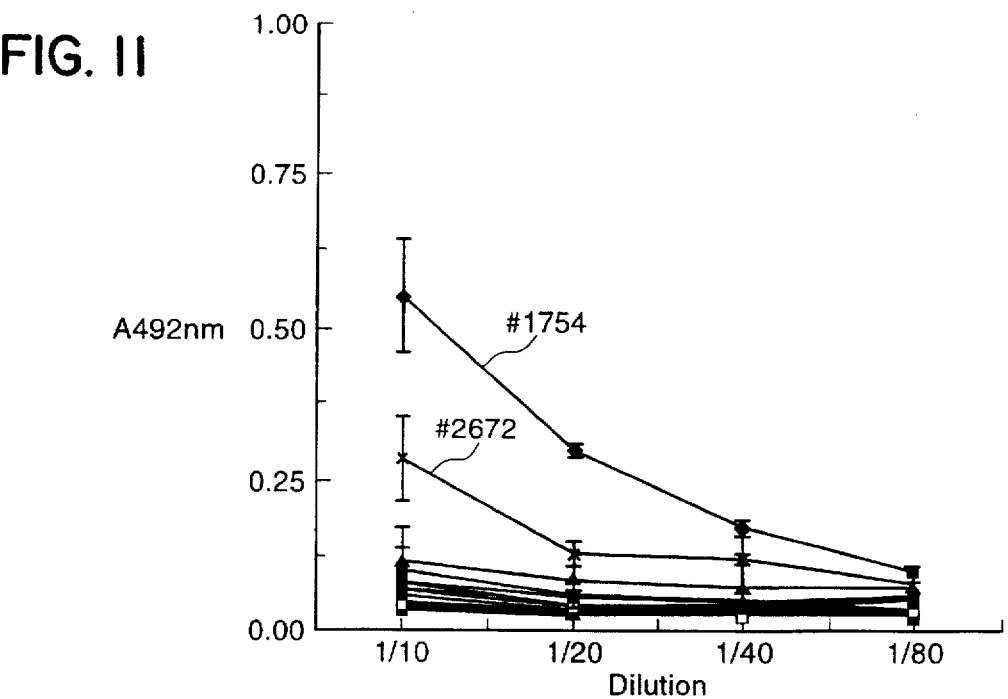
FIG. 11. This figure demonstrates that at least 10% of breast cancer patients have the antibody against mucin. Serum from breast cancer patients was reacted with the 105 amino acid synthetic peptide, and specific reactivity detected by ELISA assay. Normal serum did not react with the peptide and was used as a control. The same results were obtained with sera from pancreatice and colon cancer patients.
Figure 12:
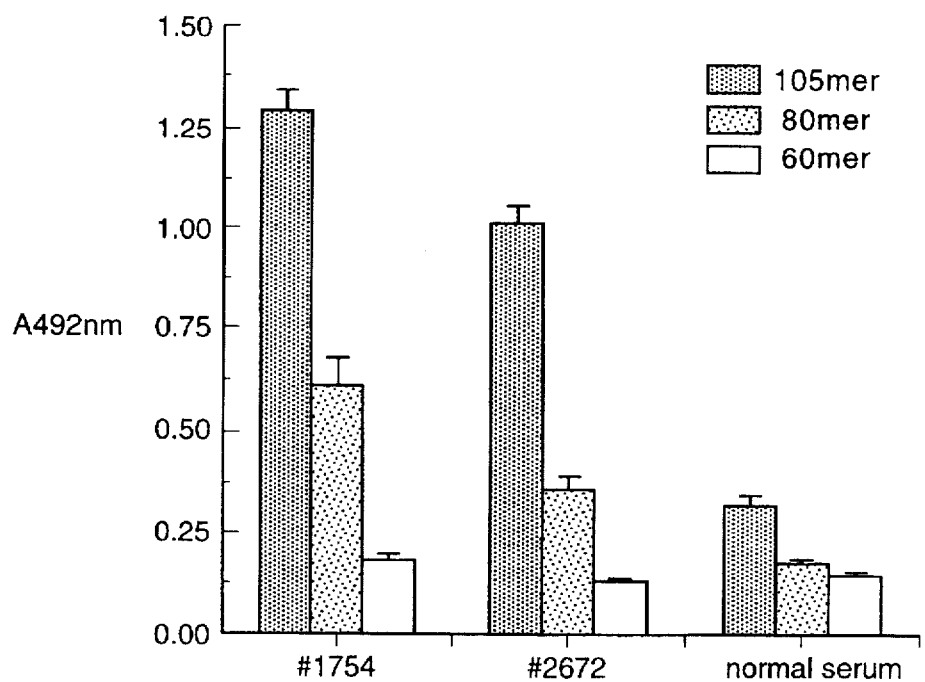
FIG. 12. This figure shows that the antibody against mucin is only detectable with the peptides of the invention, where the 105 amino acid peptide demonstrates the best results. Previous experiments performed by the inventors and others by reacting patient sera with short mucin peptides or purified mucin molecules from sera of cancer patients, detected no specific antibody.
Figure 13:
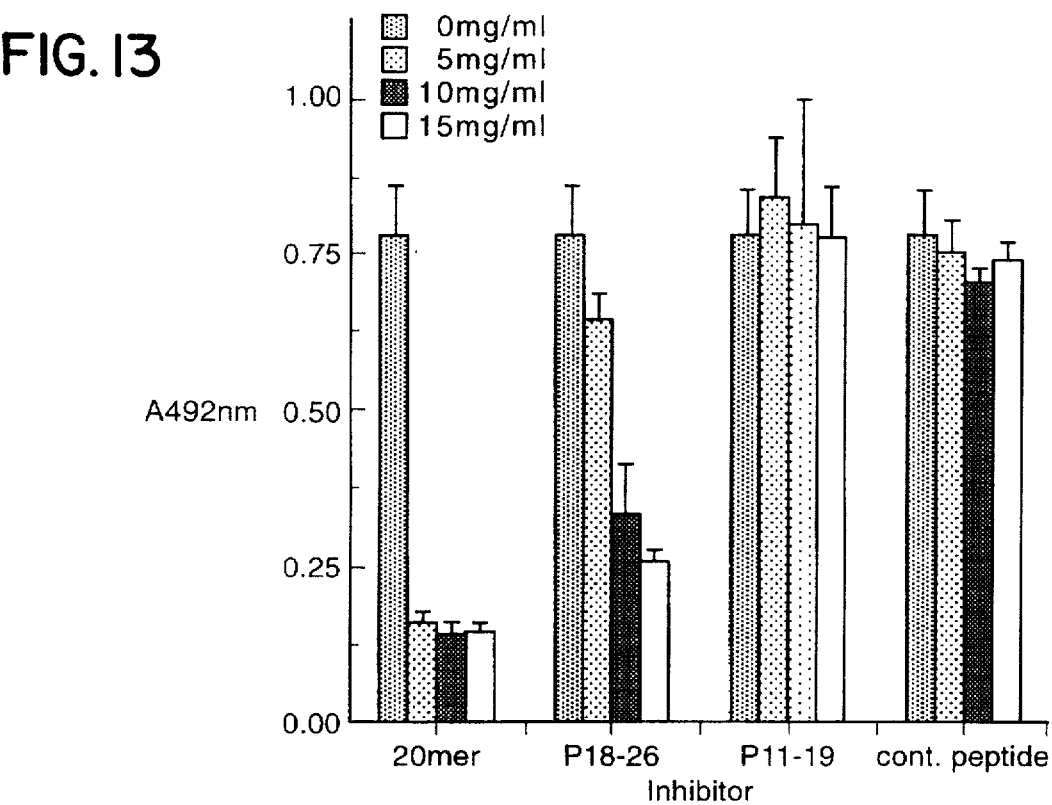
FIG. 13. This figure shows that the 105 amino acid peptide of the invention is useful in determining precisely the specificity of serum antibodies. Short peptides are used to inhibit serum reactivity with the 105 peptide. Serum is mixed first with short mucin peptides representing difference regions of the tandem repeat. The mixture is then reacted on an ELISA plate with the long 105 amino acid peptide. Short peptides with epitopes recognized by antibodies in patient's sera can interfere with the antibody binding to the long peptide.
Figure 14:
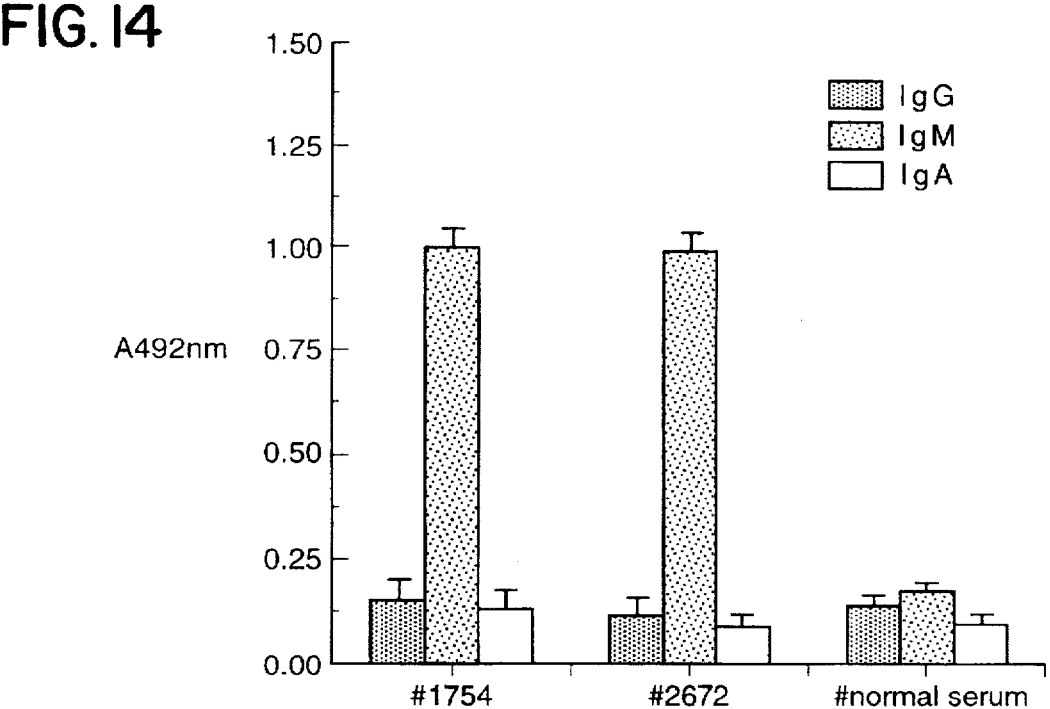
FIG. 14. This figure shows that the 105 amino acid peptide of the invention is useful in determining the precise isotype of the anti-mucin antibody. The long peptide binds the specific antibody from the patient's sera. Other antibodies are recovered by washing the ELISA plate. Secondary antibodies which are commercially available are then added. They have specific reactivities with various antibody isotypes. The end result is that antibodies from sera which bound to the 105 amino acid peptide can be determined to be either IgG, IgM, IgD, IgA or IgE, or mixtures of these. The figure shows that antibodies generated by the patients against mucinare all IgM.

FIG. 10 shows a plot of the molar ellipticity [θ] at 25° C. for the mucin 20, 60 and 105 amino acid peptides, PRN60, H2Dmuc7 and a ten amino acid control peptide (TAENAEYLRV) (SEQ ID NO:6) that does not contain proline. Clearly, the proline rich peptides exhibit dramatically greater [θ] indicating the formation of secondary structure (FIG. 10). The ratio of [θ] of the proline rich peptides to [θ] of the control peptide at 25° C. ranges from 3.2 for the mucin 20 amino acid peptide to 21.1 for the mucin 105 amino acid peptide. These enhanced [θ] with increasing numbers of mucin tandem repeats correlates with the formation of native secondary structure as detected by $^1$H-NMR spectroscopy and monoclonal antibody binding data (Fontenot et al., in press 1993A).

EXAMPLE 2

Monoclonal antibodies to native muc-1 recognized the synthetic peptides

Monoclonal antibodies may be obtained by methods well known in the art. For instance, antibodies may be obtained by immunizing mice with human tumor cells which express mucin, or with purified human mucin which was or was not stripped of sugars. Monoclonal antibodies were produced by standard Kohler Milstein hybridoma technology.

To verify that synthetic peptides corresponding to one-, two-, and three-tandem repeats of muc-1 protein core fold into the native structure, the peptides were reacted with a panel of muc-1 specific monoclonal antibodies (Table 2). These antibodies were previously shown to react with epitopes specific for the carcinoma associated form of muc-1 (Taylor-Papadimitriou, Int. J. Cancer, 49: 1–5, 1991 and Jerome, et al., Cancer Res., 52: 5985–5990, 1992). The antibodies were reacted against equal quantities of the synthetic peptides in a solid-phase ELISA. The reactivity is defined as the slope of the color change with time.

Most antibodies failed to react with a twenty amino acid peptide corresponding to one repeat and beginning with proline 1 (Table 2). However, these antibodies reacted with peptides corresponding to two- and three-tandem repeats of the protein core. A probable explanation for this is that native presentation of the predominant epitope (PDTRP) recognized by these antibodies requires at least the alanine of the previous repeat. This observation could explain the results obtained by others showing that other amino acids can be substituted for alanine, and that peptides linked to a carrier or a pin will react without alanine (Price, et al., Molecular Immunology, 27: 795–802, 1990 and Xing, et al., Immunology, 72, 1991). The increase in reactivity of the monoclonal antibodies with the 40 and 60 amino acid peptides indicates that the epitopes attain a native conformation in the absence of glycosylation, reflecting the structure seen in native mucin.

EXAMPLE 3
Mucin protein core formed a stable folded secondary structure

Figure 1A:
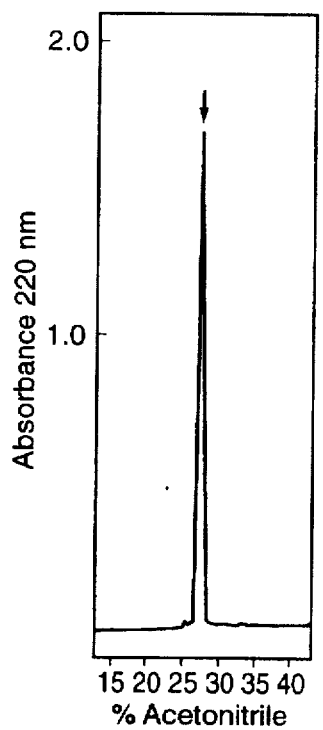
FIG. 1. The analytical HPLC chromatograms of the crude synthetic peptide products of the twenty, forty, and sixty amino acid peptides are shown above. The electrospray mass spectra of the largest HPLC peak fractions (indicated by arrow) are shown below. In each case the mass obtained was the expected molecular weight (20 mer=1886 daltons, 40 mer=3766 daltons, 60 mer=5625 daltons).
Figure 1B:
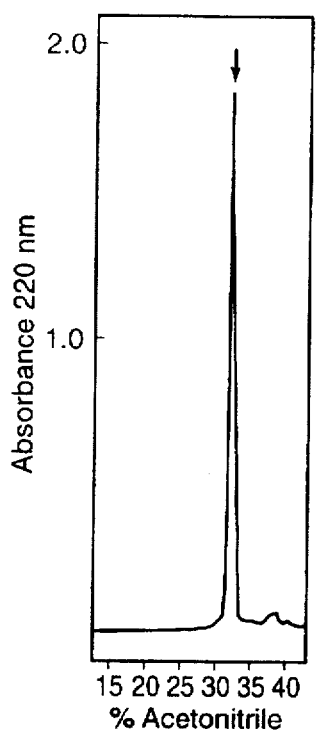
Figure 1C:
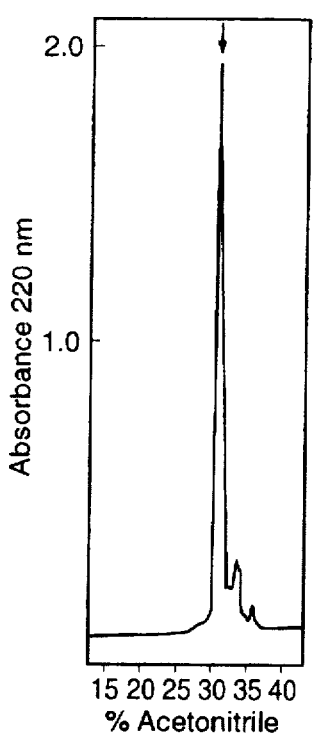
Figure 1D:
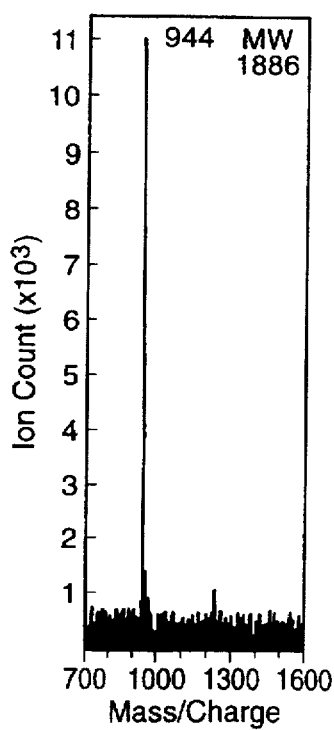
Figure 1E:
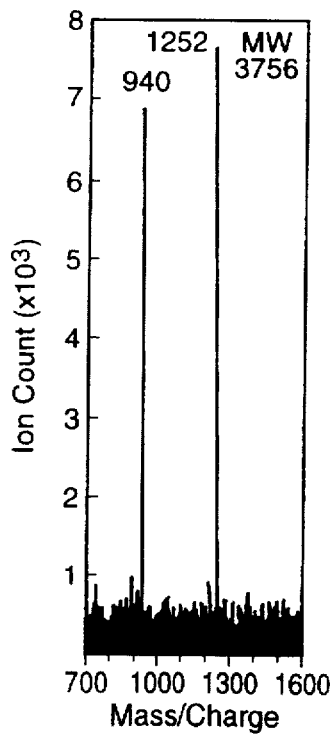
Figure 1F:
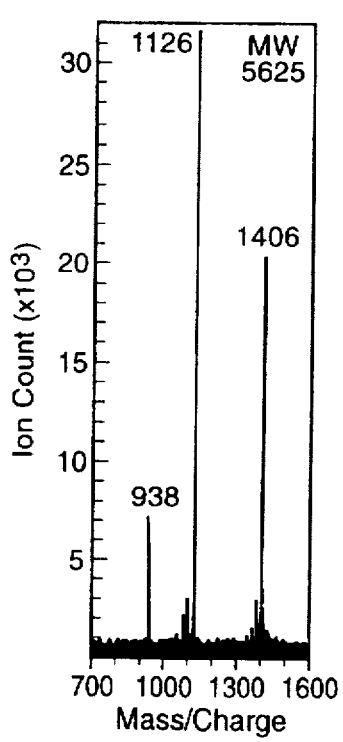
Figure 2:
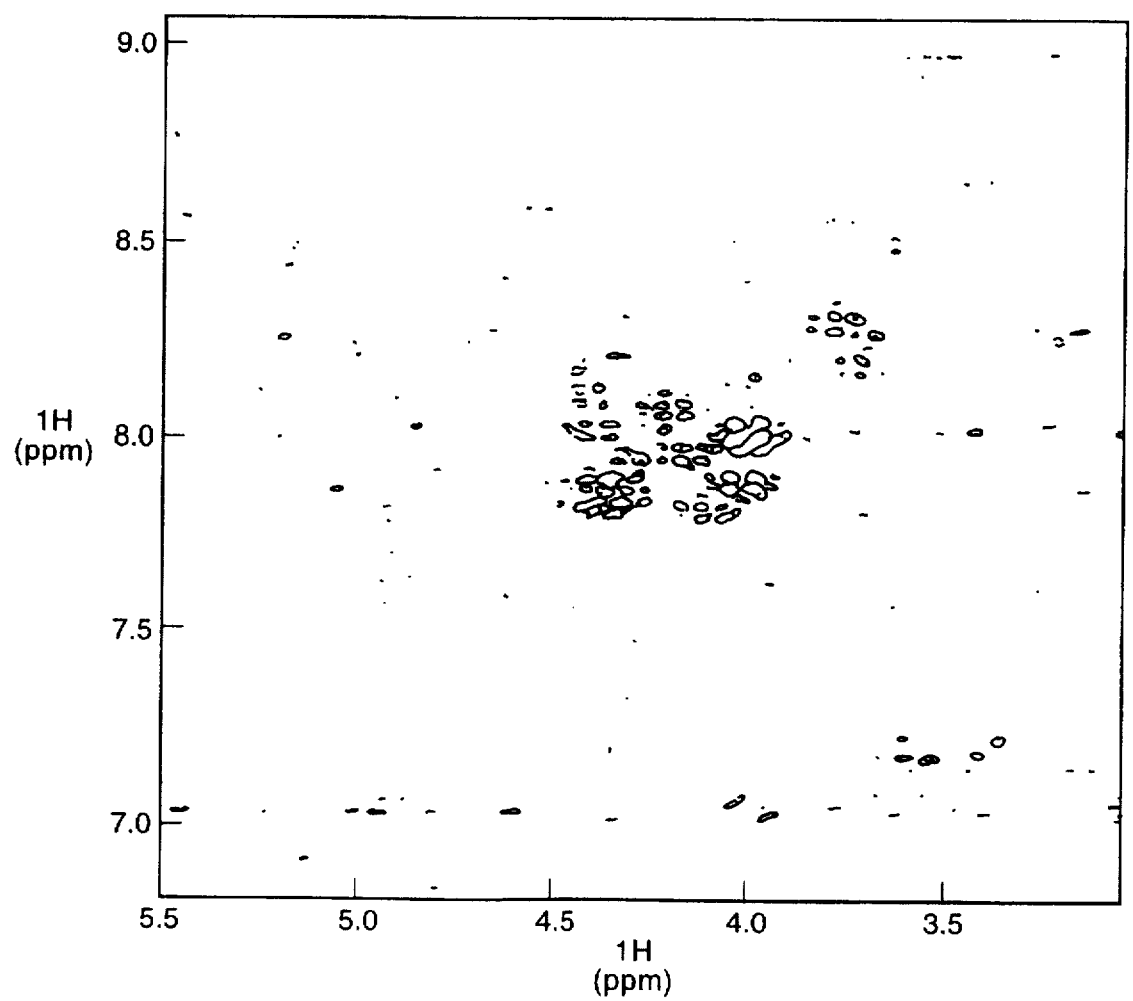
FIG. 2. 600-MHz cosy $^1$H-NMR spectra of muc-1 60 amino acid peptide dissolved in deuterated 0.1M phosphate buffer pH 7.2, in $D_2O$. The cross peaks show scalar correlation between amide-$^1$H and $^1$Hα. These amide protons are protected from exchange with the solvent by the folded structure of the mucin peptide.

A finger print region of the two-dimensional correlated spectroscopy (COSY) of the mucin 60 amino acid peptide in $D_2O$ (FIG. 2) clearly shows cross peaks of some nonexchangeable amide protons. This particular region of the spectrum shows scalar correlation between amide-$^1$H and $^1$H-alpha protons. These cross peaks did not exchange during the duration of more than 12 hours at 27° C. Thus, these amide protons appear to be protected very well inside the 3-dimensional structure of the folded mucin. This experiment clearly shows that a mucin 60 amino acid peptide retains a stable ordered structure in solution, in distinct contrast to the random coil conformation previously reported (Jentoft, Trends Biochem. Sci., 15: 291–294, 1990).

EXAMPLE 4
Development of structure requires multiple tandem repeats

FIG. 3 shows the region of the $^1$H-NMR spectrum which is characteristic of β-protons of the amino acid side chains. The muc-1 tandem repeat sequence contains only one aspartic acid (D) and one histidine (H) residue per TR, and the side chain, β-protons of these an amino acids are resolved into two distinct regions of the spectrum (Wuthrich, NMR of proteins and nucleic acids, John Wiley and Sons, New York, N.Y., 1986). FIG. 3 shows the spectrum of the free amino acids as compared to the spectrum of the synthetic peptide corresponding to one-tandem repeat, two-tandem repeat, and three-tandem repeat peptides. Arrows indicate differences in the spectra associated with increasing numbers of tandem repeats in the peptide. These spectra indicate that the development of an ordered structure depends on the number of tandem repeats (size) in the peptide. If the secondary structure of these peptides were random coil, the spectrum in this region would be expected to be independent of the number of repeats present and to correspond closely to that of the free amino acids (Wuthrich, NMR of proteins and mucleic acids, John Wiley and Sons, New York, N.Y., 1986). The data in FIG. 3 show clearly that the spectrum is dependent on the number of repeats and is significantly different from the spectra observed for free amino acids.

Free amino acids, or peptides containing one, two or three 20 amino acid repeats of muc-1 core all contain the same information when considering the $^1$HNMR responsive protons in the region of the spectrum from 1.6 to 3.3 ppm from DSS (Wuthrich, NMR of proteins and mucleic acids, John Wiley and Sons, New York, N.Y.,). Differing chemical shifts and numbers of peaks are the result of changes in the local magnetic fields arising from structural changes (folding) of the peptide backbone. Of particular interest in FIG. 3 are the distinct spectral changes occurring in the aspartic acid, β-proton resonances (2.4 to 2.7 ppm) when going from free amino acids to one-, two-, and three-tandem repeats. Similarly, structural changes are evident from the changes in the histidine β-proton resonances (2.9 to 3.3 ppm) as the number of protein tandem repeats increases. These results can be interpreted to indicate that an ordered structure is not completely formed in a peptide with only one 20 amino acid repeat, and that the larger peptides containing 2 and 3 tandem repeats contains sufficient folding information to result in a cooperative formation structure.

EXAMPLE 5
Intrinsic viscosity measurements support a folded rod-shaped structure The intrinsic viscosity [η] ml/g is a sensitive measure of the state of folding, and the molecular shape (globular vs. rod-like) of a protein (Tanford, Physical Chemistry of Macromolecules, John Wiley and Sons, New York, N.Y., pp. 798–799, 1961 and Tanford, et al., 1967). Tanford has shown that for a protein in a random coil state, the intrinsic viscosity [η] ml/g is at a maximum and is given by the equation [η] ml/g=0.684 $n^{0.67}$ where n is the number of amino acids in the protein. The random coil intrinsic viscosity of a protein depends only on the number of residues. For a 60 amino acid peptide the intrinsic viscosity value is predicted to be 10.7 ml/g. The measured value for the muc-1 synthetic peptide with 3 repeats is 7.71 ml/g (Table 3). This value of 7.71 ml/g would correspond to the expected intrinsic viscosity of a random coil 36 amino acid peptide. The measured value of intrinsic viscosity for the muc-1 peptide with 3 repeats is significantly less than expected if the peptide were random coil. Therefore, based on intrinsic viscosity, this peptide assumes an ordered conformation in solution, in agreement with the structure suggested by previous NMR experiments.

Intrinsic viscosity can also yield information about molecular shape. The intrinsic viscosity for all globular proteins is 3.3 to 3.9 ml/g and is independent of molecular weight (Tanford, Physical Chemistry of Macromolecules, John Wiley and Sons, New York, N.Y., pp. 798–799, 1961). The value of 7.71 ml/g for the muc-1 peptide with 3 repeats rules out a globular shape and is consistent with a rod-like shape with an axial ratio (length/width) of 9.2 (Cantor, et al., Biophysical Chemistry Part 2: Techniques for the Study of Biological Structure and Functions, W. H. Freeman and Co., New York, N.Y., 1980). This measured axial ratio value (9.2) is in agreement with the value of 9.7 determined from the molecular graphics program SYBYL in which the peptide sequence was modeled as series of type I reverse turns (Table 3).

It can be concluded from the intrinsic viscosity value that the peptide with 3 repeats forms an ordered conformation in solution that is rod-like in shape with a longitudinal span of 33–34 A/repeat. This result suggests that the unglycosylated protein core could determine the extended structure seen in electron micrographs (Lan, et al., J. Biol. Chem., 262: 12863–12870, 1987). These results also support the hypothesis that the muc-1 protein core exists as a poly-proline β-turn helix.

EXAMPLE 6
Model of a poly-proline β-turn helix for muc-1 TR domain

Figure 7:
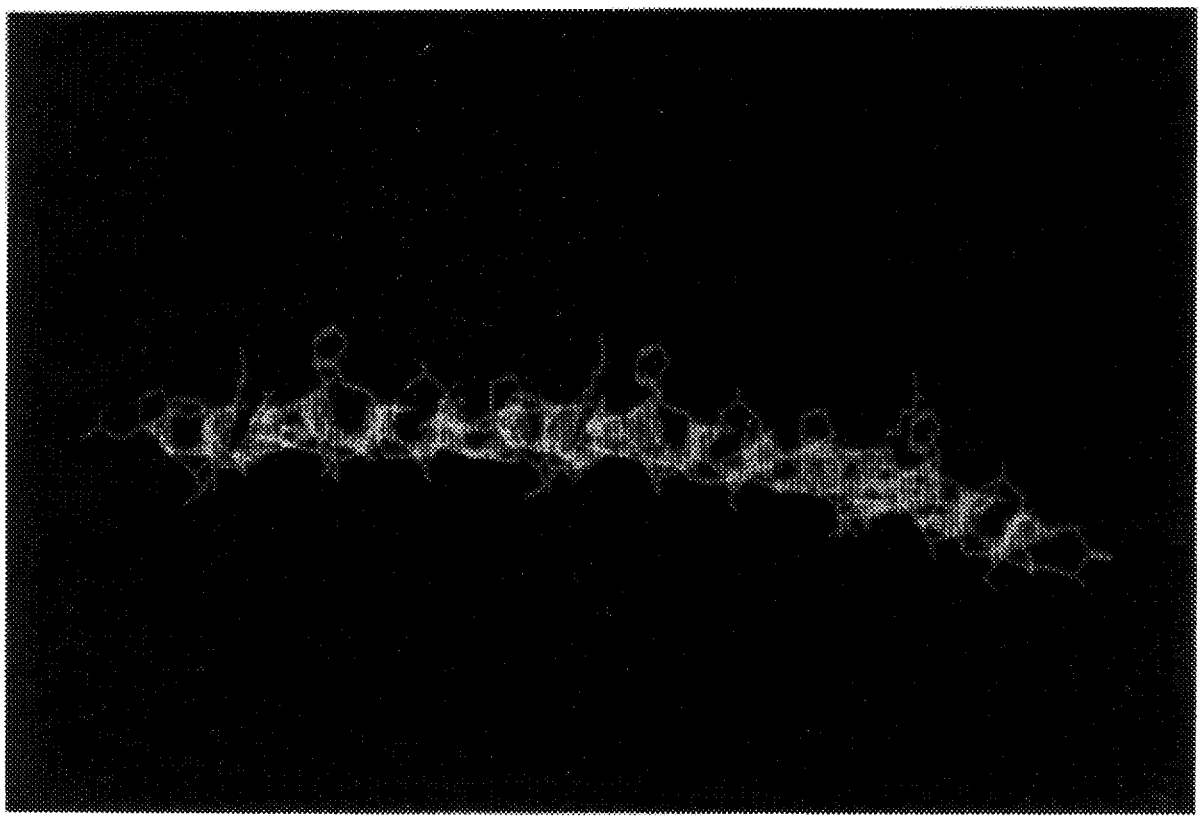
FIG. 7. The sequence of three-tandem repeats of the human mucin muc-1 gene modeled into a poly-type I turn conformation using the Tripos molecular graphics program SYBYL.

FIG. 7 shows a computer model of the sixty amino acid peptide in the poly-proline β-turn helix conformation that was created by assuming that the mucin sequence exists in a poly-type I turn conformation. This model reveals that the amino acid side chains radiate outward from an extended rod-like backbone, and are completely exposed to the solvent (FIG. 7). This orientation of the side chains facilitates accessibility of potential glycosylation sites to the glycosylation machinery. The secondary structure is not necessarily dependent on glycosylation, nor does it have to be disrupted by the addition of carbohydrate. This model explains the lack of effect that heating the peptides has on the NMR spectrum. Since no unfolding can occur in the globular sense with side chains moving from a buried hydrophobic core to an aqueous exterior, there are no large chemical shifts of the side-chain protons upon heating (Price, et al., Molecular Immunology, 27: 795–802, 1990). The model also explains why the A and DT residues will permit substitution within the primary epitope of APDTRP. When the turn is formed, the P and R amino acid side chains are in the same space and accessible for binding to the antibody. Substitutions that allow the turn to form will be tolerated.

The entire contents of all references cited herein above are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A synthetic muc-1 peptide 105 amino acids in length comprising five sequential 20-amino acid tandem repeats of muc-1 and five additional amino acids, which five additional amino acids either precede the first of the five sequential 20-amino acid tandem repeats or follow the fifth of the five sequential 20-amino acid tandem repeats, wherein said synthetic muc-1 peptide attains native conformation in the absence of glycosylation.

2. A composition comprising at least one synthetic muc-1 peptide according to claim 1 covalently linked to a pharmaceutically acceptable carrier molecule.

3. An immunogenic composition capable of inducing a mammal to produce antibodies specific for an amino acid sequence corresponding to an epitope present on a cancer cell that does not express muc-1, wherein said immunogenic composition comprises a synthetic peptide comprising at least two 20-amino acid tandem repeats of muc-1 and at least one foreign amino acid sequence corresponding to an epitope present on a cancer cell that does not express muc-1, which foreign amino acid sequence is inserted as a substitution within an amino acid sequence PDTRP in the at least two 20-amino acid tandem repeats of muc-1, wherein said synthetic peptide attains native conformation in the absence of glycosylation and when the foreign amino acid sequence is present in the synthetic peptide.

4. The immunogenic composition according to claim 3, wherein said synthetic peptide is 105 amino acids in length and comprises five sequential 20-amino acid tandem repeats of muc-1 and five additional amino acids, which five additional amino acids either precede the first of the five sequential 20-amino acid tandem repeats or follow the fifth of the five sequential 20-amino acid tandem repeats, and at least one foreign amino acid sequence corresponding to an epitope present on a cancer cell that does not express muc-1, which foreign amino acid sequence is inserted as a substitution within an amino acid sequence PDTRP in the at least five sequential 20-amino acid tandem repeats of muc-1.

5. A method of producing immunity to cancer that does not express muc-1, comprising the step of administering the immunogenic composition according to claim 3 to a mammal in an immunogenically effective amount.

6. A cancer vaccine comprising a synthetic peptide comprising at least two 20-amino acid tandem repeats of muc-1 and at least one foreign amino acid sequence corresponding to an epitope present on a cancer cell that does not express muc-1, which foreign amino acid sequence is inserted as a substitution within an amino acid sequence PDTRP in the at least two 20-amino acid tandem repeats of muc1, wherein said synthetic peptide attains native conformation in the absence of glycosylation and when the foreign amino acid sequence is present in the synthetic peptide.

7. The cancer vaccine according to claim 6, wherein said synthetic peptide is 105 amino acids in length comprising five sequential 20-amino acid tandem repeats of muc-1 and five additional amino acids, which five additional amino acids either precede the first of the five sequential 20-amino acid tandem repeats or follow the fifth of the five sequential 20-amino acid tandem repeats, and at least one foreign amino acid sequence corresponding to an epitope present on a cancer cell that does not express muc-1, which foreign amino acid sequence is inserted as a substitution within an amino acid sequence PDTRP in the five sequential 20-amino acid tandem repeats of muc-1.

8. A method of producing immunity to a cancer that does not express muc-1, comprising the step of administering the vaccine according to claim 6 to a mammal in an immunogenically effective amount.

9. An immunogenic composition capable of inducing in a mammal antibodies against a cancer epitope of a cancer that expresses muc-1 which comprises a synthetic peptide 105 amino acids in length comprising five 20-amino acid tandem repeats of muc-1 and five additional amino acids, which five additional amino acids either precede the first of the five sequential 20-amino acid tandem repeats or follow the fifth of the five sequential 20-amino acid tandem repeats, wherein said synthetic muc-1 peptide attains native conformation in the absence of glycosylation.

10. A method of producing immunity to cancer that expresses muc-1, comprising the step of administering the immunogenic composition according to claim 9 to a mammal in an immunogenically effective amount.

11. A cancer vaccine for a cancer that expresses muc-1, comprising a synthetic muc-1 peptide 105 amino acids in length, which comprises five 20-amino acid tandem repeats of muc-1 and 5 additional amino acids, which five additional amino acids either precede the first of the five sequential 20-amino acid tandem repeats or follow the fifth of the five sequential 20-amino acid tandem repeats, and said synthetic muc-1 peptide attains native conformation in the absence of glycosylation.

* * * * *